(12) United States Patent
Berberich et al.

(10) Patent No.: US 12,370,539 B2
(45) Date of Patent: Jul. 29, 2025

(54) CONTROL DEVICE FOR AUTOMATED PIPETTING SYSTEMS

(71) Applicant: BRAND GMBH & CO KG, Wertheim (DE)

(72) Inventors: Christian Berberich, Neunkirchen (DE); David Scholten, Faulbach (DE)

(73) Assignee: BRAND GMBH & CO KG, Wertheim (DE)

( * ) Notice: Subject to any disclaimer, the term of this patent is extended or adjusted under 35 U.S.C. 154(b) by 1235 days.

(21) Appl. No.: 16/880,035

(22) Filed: May 21, 2020

(65) Prior Publication Data

US 2020/0368739 A1 Nov. 26, 2020

(30) Foreign Application Priority Data

May 21, 2019 (DE) .................... 10 2019 113 531.1

(51) Int. Cl.
*B01L 3/02* (2006.01)
*B01L 9/00* (2006.01)
*G01N 35/00* (2006.01)
*G01N 35/10* (2006.01)
*G05B 19/042* (2006.01)

(52) U.S. Cl.
CPC ............. *B01L 3/0286* (2013.01); *B01L 3/021* (2013.01); *G01N 35/00722* (2013.01); *G01N 35/1016* (2013.01); *G05B 19/0425* (2013.01); *B01L 2200/087* (2013.01); *B01L 2300/027* (2013.01); *B01L 2300/0829* (2013.01); *G01N 2035/0091* (2013.01)

(58) Field of Classification Search
None
See application file for complete search history.

(56) References Cited

U.S. PATENT DOCUMENTS

| | | | |
|---|---|---|---|
| 6,659,142 B2 * | 12/2003 | Downs .................... | B01F 33/84 141/2 |
| 8,669,112 B2 * | 3/2014 | Heinonen ............ | G01N 35/028 422/63 |
| 10,422,806 B1 * | 9/2019 | Patel ...................... | G01N 33/82 |

(Continued)

FOREIGN PATENT DOCUMENTS

| EP | 3 171 177 A1 | 5/2017 |
|---|---|---|
| WO | 2017143182 A2 | 8/2017 |

*Primary Examiner* — Elizabeth A Robinson
*Assistant Examiner* — Brittany I Fisher
(74) *Attorney, Agent, or Firm* — Calderon Safran & Wright P.C.; David S. Safran

(57) ABSTRACT

A computer-implemented control device for controlling an automated pipetting system. The control device is designed to control at least one actuator for moving a pipetting apparatus between receptacle devices for liquids that are to be pipetted. The control device is designed, so as, before the execution of multiple specified transfer steps by the pipetting apparatus and the actuator, to analyze the specified order of execution of these transfer steps and the liquid to be pipetted in these transfer steps and, after the analysis, to alter the order of execution of these transfer steps and/or to combine multiple instances of these transfer steps automatically. Additionally, an automated pipetting system has such a control device, and a method for controlling the automated pipetting system are provided.

14 Claims, 13 Drawing Sheets

(56) References Cited

U.S. PATENT DOCUMENTS

| | | | |
|---|---|---|---|
| 10,449,534 B2 | 10/2019 | Berberich et al. | |
| 2004/0142486 A1 | 7/2004 | Weselak et al. | |
| 2014/0305227 A1* | 10/2014 | Johns | B04B 13/00 73/863.01 |
| 2015/0072889 A1* | 3/2015 | Lui | C12Q 1/705 435/6.12 |
| 2016/0139166 A1* | 5/2016 | Berberich | G01N 35/1016 435/6.12 |
| 2018/0340949 A1 | 11/2018 | Maetzler et al. | |
| 2019/0291116 A1* | 9/2019 | Amorese | G01N 35/1065 |
| 2019/0358626 A1* | 11/2019 | Romer | G01F 11/029 |

\* cited by examiner

CONTROL DEVICE FOR AUTOMATED PIPETTING SYSTEMS

BACKGROUND OF THE INVENTION

Field of the Invention

The invention relates to a computer-implemented control device for controlling an automated pipetting system, to an automated pipetting system having such a control device, to a method for controlling an automated pipetting system, to a computer program product, and to the use of a control device for controlling an automated pipetting system.

An automated pipetting system within the context of the present invention is preferably an apparatus designed for fully automatic liquid transfer. To this end, the automated pipetting system preferably has a pipetting apparatus that is movable in multiple spatial directions. In principle, however, the control device according to the present invention can also be used for other apparatus, in particular for other automated laboratory systems, in particular for repositioning substances or items.

An automated pipetting system of the type in question is preferably designed to move a pipetting apparatus, also called pipetting head or liquid end, between different operating positions. To this end, the automated pipetting system can have a positioning device, in particular an X/Y/Z moving device, by means of which the pipetting apparatus can be moved. The positioning device can also be or have a robot arm by means of which the pipetting apparatus is at least substantially freely movable in space.

A pipetting apparatus within the context of the present invention is preferably a movable head having one or more displacer units or other devices for generating overpressure or underpressure to aspirate or expel liquids. The pipetting apparatus preferably has one or more coupling points for installing or replacing one or more pipette tips or syringes. The respective pipette tips or coupling points have, preferably respective, displacer units. The syringe or the respective syringes is/are preferably in the form of a displacer unit or form such a displacer unit.

The pipetting apparatus can have one or more pipette tips or syringes at one or more coupling points, pipetting apparatus having just a single pipette tip or syringe being referred to as single-channel pipetting apparatus and a pipetting apparatus having multiple pipette tips or syringes being referred to as a multichannel pipetting apparatus.

The text below deals with the pipetting apparatus in the version with pipette tips. The displacer unit(s) thereof more often than not has/have one or more cylinder-piston arrangements, designed to aspirate or expel liquid through the orifice(s) of the pipette tip(s) into or from the latter. In principle, the aspiration and expulsion of liquid into or from the respective pipette tip can also take place in another way, however.

The automated pipetting system preferably has receptacle devices for liquids that are to be pipetted or is designed to receive or hold such receptacle devices, in particular what are known as wells or the like. A receptacle device within the context of the present invention is preferably a vessel, a recess, indentation, depression and/or predefined position, the receptacle device being designed to receive and provide liquid to be pipetted.

The automated pipetting system preferably has an actuator or multiple actuators by means of which the pipetting apparatus is moved or movable between different receptacle devices and/or by means of which an intake of liquid into and/or a delivery of liquid from one or more of the pipette tips of the pipetting apparatus can be achieved. These or further actuators of the automated pipetting system are preferably controllable by a control device.

An actuator within the context of the present invention is preferably a device for the controlled achievement of an effect for operating the automated pipetting system. In particular, the actuator is a motor or other drive for moving the pipetting apparatus and/or a drive for moving the piston of a cylinder-piston arrangement or other displacer unit in order to aspirate or expel liquid into or from a pipette tip through an orifice of the latter.

A well within the context of the present invention is preferably a graphical means for representing at least one receptacle device in a configuration interface displayable or displayed by the display device. The respective well corresponds to a specific receptacle device of the automated pipetting system, in particular in its shape and/or position or orientation with respect to other receptacle devices or wells. Particularly preferably, the receptacle devices of the automated pipetting system to be controlled are schematically presented, displayable or represented by means of the wells in the configuration interface.

The control device is designed so that, to specify at least one transfer volume to be received and at least one transfer volume to be delivered for at least one transfer step, a transfer parameter corresponding to the transfer volume to be received and/or to be delivered is stipulable in the configuration interface by means of the input device.

The transfer volume is preferably a specific volume of liquid that is supposed to be received from the respective receptacle device or is supposed to be delivered to the respective receptacle device. The transfer volume can be a volume of liquid to be received or to be taken, that is to say a volume of the liquid to be pipetted that needs to be taken from a receptacle device and/or needs to be received in, in particular needs to be aspirated into, a pipette tip or syringe. The terms transfer volume "to be received" and transfer volume "to be taken" are preferably synonymous and interchangeable. Alternatively or additionally, the transfer volume can be a volume to be delivered, that is to say a volume to be conveyed from a pipette tip or syringe and/or a volume of the liquid to be pipetted that needs to be delivered to the receptacle device. Transfer volumes to be received and to be delivered can be distinguished, for example by an arithmetic sign or another identification of the transfer parameter or transfer volume.

Multiple source wells and multiple destination wells are selectable in the configuration interface by means of the input device. The known control device is designed so that, to specify multiple transfer steps and the order of execution thereof by the pipetting apparatus and the actuator, multiple previously selected source wells are assignable in the configuration interface to at least one destination well by selecting this destination well. Preferably, the specifying of transfer steps also stipulates the order of execution thereof by the pipetting apparatus and the actuator.

In many transfer steps, the respective liquid in the receptacle devices must not be polluted by a different liquid. When liquid is taken from a receptacle device and, to this end, received in an interchangeable pipette tip or syringe and this liquid is delivered to a further receptacle device and, to this end, expelled from the pipette tip or syringe, the pipette tip or syringe is wetted on the outside and inside. If this pipette tip or syringe is dipped into a different liquid in a subsequent transfer step, this already causes pollution of this other liquid. To avoid this, the pipette tip or syringe is changed in principle before every transfer step in which a different liquid from in the immediately preceding transfer step needs to be pipetted. To this end, the pipetting apparatus is moved to a container by means of the actuator and the pipette tip or syringe used in the immediately preceding transfer step is detached from the pipetting apparatus and discarded into the container. Subsequently, the pipetting apparatus is moved to a magazine by means of the actuator and a new pipette tip or syringe is taken from the magazine and detachably mounted on the pipetting apparatus. The change of pipette tip or syringe thus costs time, consumes materials and creates refuse that needs to be disposed of.

Description of Related Art

European Patent Application EP 3 021 123 A1 and corresponding U.S. Pat. No. 10,449,534 B2, on which the present invention is based, show a computer-implemented control device for controlling an automated pipetting system of the type in question so that the features and explanations described below therefore also apply to the present invention.

The known control device, like the control device according to the invention, is designed to control at least one actuator for moving a pipetting apparatus between receptacle devices for liquids that are to be pipetted. The control device is designed to control the pipetting apparatus such that a specific transfer volume of liquid is receivable from at least one of the receptacle devices, and at least a portion of the transfer volume of liquid is deliverable to at least one other of the receptacle devices, by means of the pipetting apparatus in a transfer step.

In a transfer step, a specific transfer volume of liquid is thus received by the pipetting apparatus from one or more of the receptacle devices and at least a portion of the transfer volume of liquid is delivered by the pipetting apparatus to one or more other of the receptacle devices. If, after the delivery of a liquid, a liquid is again received by the pipetting apparatus, then this receiving of liquid is already part of a further (new, separate) transfer step. The moving of the pipetting apparatus from the receptacle device from which liquid was most recently delivered to the receptacle device from which liquid is taken next can be ascribed to the further transfer step.

The known control device has an input device and a display device. At least one configuration interface is displayable by the display device. An input device within the context of the present invention is preferably a keyboard, a computer mouse, a trackball, a touchscreen, a camera, a sensor or another device for controlling, or for data input into, a computer or the like. A display device is preferably a monitor, a display, a touchscreen, a projector or another device for displaying a graphical user interface, in particular one or more configuration interfaces.

The control device can have at least one memory device, in particular a main memory and/or a read-only memory such as a hard disk, and/or a processor. Further, the control device preferably has an interface designed to control the actuator(s) of the automated pipetting system.

The control device is designed so that the receptacle devices are represented in the configuration interface by graphically depicted wells. The receptacle devices from which liquid to be pipetted is supposed to be received by the pipetting apparatus correspond to source wells. The receptacle devices to which liquid to be pipetted is supposed to be delivered by the pipetting apparatus correspond to destination wells.

SUMMARY OF THE INVENTION

The present invention is based on the problem of improving the known automated pipetting system in respect of materials consumption, in particular the consumption of pipette tips or syringes, and/or the time required for carrying out the specified transfer steps.

The above problem is solved for a control device, by an automated pipetting system, and a method for controlling an automated pipetting system, by a computer program product, and by the manner of use thereof as described herein.

The control device according to the invention having the features described above in relation to said European Patent Application EP 3 021 123 A1 and corresponding U.S. Pat. No. 10,449,534 B2 have provision for the control device to be designed so as,
to analyze the specified order of execution of these transfer steps and the liquid to be pipetted in these transfer steps before the execution of multiple specified transfer steps by the pipetting apparatus and the actuator, and
after the analysis, to alter the order of execution of these transfer steps and/or to combine multiple instances of these transfer steps automatically.

The analyzing can, e.g., have provision for the control device to look for transfer steps in accordance with which identical liquids need to be pipetted. Within the context of the present invention, liquids are identical if their chemical composition and/or possibly concentration is/are concordant. The volume to be pipetted is not critical. It is also possible for liquids to be able to be prescribed or defined as identical and/or miscible.

The analyzing involves transfer steps (e.g., those in accordance with which identical liquids need to be pipetted) being examined by the control device for whether these transfer steps are independent of other transfer steps, or these transfer steps can be executed in an order other than that specified. A transfer step may have become dependent as a result of a change, scheduled in the specified order, of the liquid to be pipetted itself or as a result of a specified mixing with a different liquid, for example.

The control device according to the invention is designed so as, after the analysis but before the execution of the specified transfer steps—typically, on the basis of the analysis results—to alter the order of execution of these transfer steps and/or to combine multiple instances of these transfer steps automatically. This allows the order of execution of these transfer steps to be altered and/or a combining of transfer steps to be performed automatically without differently arranging, or differently positioning, receptacle devices and/or liquid in the receptacle devices. As such, the time required for executing these transfer steps and/or the materials consumption, in particular the consumption of pipette tips or syringes, can be reduced.

The combining of transfer steps involves pipetting processes (receiving or delivering a specific transfer volume of liquid by means of the pipetting apparatus) that, before the combining, were specified as needing to be executed in multiple (separate) transfer steps being specified as needing to be performed in one transfer step.

Exemplary Scenario 1

If, e.g., three transfer steps are specified:
according to the first transfer step, a specific transfer volume of liquid is supposed to be received from a first receptacle device and the transfer volume of liquid is supposed to be delivered to a second receptacle device,
according to the second transfer step, a specific transfer volume of liquid is supposed to be received from the first receptacle device and the transfer volume of liquid is supposed to be delivered to a third receptacle device, and
according to the third transfer step, a specific transfer volume of liquid is supposed to be received from the first receptacle device and the transfer volume of liquid is supposed to be delivered to a fourth receptacle device,
then the progressive execution of these transfer steps results in the pipetting apparatus being, among other things:
moved to the first receptacle device, moved from the first to the second receptacle device,
moved from the second to the first receptacle device, moved from the first to the third receptacle device, and
moved from the third to the first receptacle device and moved from the first to the fourth receptacle device.

Combining these three transfer steps means that, instead of them, one transfer step is specified, in accordance with which:
the sum of the specific transfer volumes of liquid that is supposed to be received from the first receptacle device and a respective portion of the transfer volume of liquid that is supposed to be delivered to the second, third and fourth receptacle devices in succession.

As such, the execution of this transfer step results in the pipetting apparatus being moved to the first receptacle device, moved from the first to the second receptacle device, moved from the second to the third receptacle device and moved from the third to the fourth receptacle device, among other things.

The execution of this transfer step results in the pipetting apparatus being moved a significantly shorter distance, which saves energy and time. This applies all the more if the first receptacle device is further away from the third and fourth receptacle devices than the second receptacle device is from the third and fourth receptacle devices.

Exemplary Scenario 2

If, e.g., three transfer steps are specified, wherein:
according to the first transfer step, a specific transfer volume of liquid is supposed to be received from a first receptacle device and the transfer volume of liquid is supposed to be delivered to a second receptacle device,
according to the second transfer step, a specific transfer volume of liquid is supposed to be received from a third receptacle device and the transfer volume of liquid is supposed to be delivered to the second receptacle device, and
according to the third transfer step, a specific transfer volume of liquid is supposed to be received from a fourth receptacle device and the transfer volume of liquid is supposed to be delivered to the second receptacle device,
then the progressive execution of these transfer steps results in the pipetting apparatus being, among other things,
moved to the first receptacle device, moved from the first to the second receptacle device,
moved from the second to the third receptacle device, moved from the third to the second receptacle device, and
moved from the second to the fourth receptacle device and moved from the fourth to the second receptacle device.

Combining these three transfer steps means that, instead of them, one transfer step is specified, in accordance with which a specific transfer volume of liquid is supposed to be received from the first, third and fourth receptacle devices in immediate succession and the whole of the received transfer volume of liquid is supposed to be delivered to the second receptacle device in precisely one pipetting process.

As such, the execution of this combined transfer step results in the pipetting apparatus being moved to the first receptacle device, moved from the first to the third receptacle device, moved from the third to the fourth receptacle device and moved from the fourth to the second receptacle device, among other things.

The execution of this combined transfer step results in the pipetting apparatus being moved a significantly shorter distance, which saves energy and time. This applies all the more if the second receptacle device is further away from the third and fourth receptacle devices than the first receptacle device is from the third and fourth receptacle devices.

Further Embodiments of the Combining of Transfer Steps

Preferably, the control device is designed to combine transfer steps by virtue of transfer steps in accordance with which a specific transfer volume of liquid is supposed to be received from the same receptacle device as source and delivered to specific receptacle devices as destinations being automatically replaced with a transfer step in accordance with which the sum of the specific transfer volumes of liquid is supposed to be received from the source on a single occasion and the respective specific transfer volume of liquid is supposed to be delivered to the respective destination.

Alternatively or additionally, the control device can be designed to combine transfer steps by virtue of transfer steps in accordance with which a specific transfer volume of liquid is supposed to be received from specific receptacle devices as sources and delivered to a further receptacle device as the same destination being automatically replaced with a transfer step in accordance with which the respective specific transfer volume of liquid is supposed to be received from the respective source in immediate succession and the sum of the specific transfer volumes of liquid is supposed to be delivered to the destination on a single occasion.

In all scenarios and embodiments, the analyzing can alternatively or additionally have provision for the control device to look for transfer steps in accordance with which liquids are supposed to be mixed, that is to say a first liquid from a first receptacle device is supposed to be delivered to a second receptacle device in which a second liquid or a mixture of liquids is already supposed to be because the second liquid or the mixture of liquids is supposed to be delivered to the second receptacle device in one or more preceding transfer steps. The analysis also involves the control device looking for these preceding transfer steps and for transfer steps in accordance with which mixed liquids are supposed to be transferred from the second receptacle device to a third receptacle device.

This analysis can also be used by the control device so as, before the execution of the specified transfer steps, to take the analysis results as a basis for altering the order of execution of these transfer steps and/or combining multiple instances of these transfer steps automatically. This allows the time required for executing these transfer steps and/or the materials consumption, in particular the consumption of pipette tips or syringes, to be reduced.

The control device can also be designed to determine transfer steps with compatible liquids during the analysis of the transfer steps. When liquids are compatible, mixing or combining or contact does not result in unwanted pollution. Compatible liquids can be combined e.g. in one or more transfer steps. Compatible liquids can each be present as a mixture, differing in their concentration.

Preferably, the display device is designed to present source and/or destination wells having compatible liquids in the configuration interface in a visually distinguishable manner.

It is preferred if the control device is designed to alter the order of execution of these transfer steps automatically such that transfer steps in accordance with which liquid is supposed to be received from the same receptacle device or delivered to the same receptacle device are immediately successive. Optionally, the then immediately successive transfer steps can also be automatically combined by the control device. It is particularly preferred if the control device is designed to prompt a change of tip of the pipetting apparatus immediately after the immediately successive transfer steps or the combined transfer steps.

In this way, the number of tip changes can be reduced. This allows the time required for executing the transfer steps and the number of tips consumed to be reduced.

It has been found to be advantageous if the control device is designed to alter the order of execution of these transfer steps automatically such that transfer steps in accordance with which liquid is supposed to be delivered to the same receptacle device and the resultant liquid is supposed to be received from this receptacle device and delivered to a different receptacle device are immediately successive. It is particularly advantageous if the control device is designed to prompt a change of tip of the pipetting apparatus immediately after the immediately successive transfer steps.

In this way too, the number of tip changes can be reduced, this in turn allowing the time required for executing the transfer steps and the number of tips consumed to be reduced.

Preferably, the control device is designed to control the pipetting apparatus and the actuator such that a change of tip of the pipetting apparatus is performed:
  immediately after a combined transfer step and/or
  after a transfer step with one liquid and before a subsequent transfer step with a different liquid.

Preferably, the display device is designed to display the altered order of the transfer steps and/or a changed transfer volume in the configuration interface and/or to display the sequence of the transfer steps in a further configuration interface.

Advantageously, before or after the analysis of the transfer steps, transfer steps are excludable from the analysis of the control device, or multiple different liquids are selectable as needing to be mixed for the analysis of the transfer steps, in the configuration interface by means of the input device.

The proposed control device affords the advantage of convenient, fast and reliable control of the automated pipetting system.

A further, also independently realizable, aspect of the present invention relates to an automated pipetting system having the control device described above, wherein the automated pipetting system has at least one actuator for moving the pipetting apparatus between the receptacle devices, the actuator being controllable by the control device.

A further, also independently realizable, aspect of the present invention relates to the use of the control device described above for controlling the illustrated automated pipetting system.

A further, also independently realizable, aspect of the present invention relates to a method for controlling an automated pipetting system by means of a control device to control at least one actuator for moving a pipetting apparatus between receptacle devices for liquids that are to be pipetted.

The control device is designed to control the pipetting apparatus such that a specific transfer volume of liquid is receivable from at least one of the receptacle devices, and at least a portion of the transfer volume of liquid is deliverable to at least one other of the receptacle devices, by means of the pipetting apparatus in a transfer step.

The control device has an input device and a display device. At least one configuration interface is displayed by the display device. The receptacle devices are represented in the configuration interface by graphically depicted wells.

The receptacle devices from which liquid to be pipetted is supposed to be received by the pipetting apparatus correspond to source wells, and the receptacle devices to which liquid to be pipetted is supposed to be delivered by the pipetting apparatus correspond to destination wells.

Multiple source wells and multiple destination wells are selectable in the configuration interface by means of the input device. To specify multiple transfer steps and the order of execution thereof by the pipetting apparatus and the actuator, multiple previously selected source wells are assigned in the configuration interface to at least one destination well by selecting this destination well.

According to the invention, there is provision for, before the execution of multiple specified transfer steps by the pipetting apparatus and the actuator, the control device to analyze the specified order of execution of these transfer steps and the liquid to be pipetted in these transfer steps. After the analysis, the control device alters the order of execution of these transfer steps and/or combines multiple instances of these transfer steps automatically.

Preferably, the control device determines transfer steps with compatible liquids during the analysis. It is particularly preferred if the display device presents source and/or destination wells having compatible liquids in the configuration interface in a visually distinguishable manner.

In a preferred embodiment, the control device alters the order of execution of these transfer steps automatically such that transfer steps in accordance with which liquid is supposed to be received from the same receptacle device or delivered to the same receptacle device are immediately successive. A change of tip of the pipetting apparatus is preferably performed immediately thereafter.

In a further preferred embodiment, the control device alters the order of execution of these transfer steps automatically such that transfer steps in accordance with which liquid is supposed to be delivered to the same receptacle device and the resultant liquid is supposed to be received from this receptacle device and delivered to a different receptacle device are immediately successive. A change of tip of the pipetting apparatus is preferably performed immediately thereafter.

In a further preferred embodiment, the control device combines transfer steps by virtue of transfer steps in accordance with which a specific transfer volume of liquid is supposed to be received from the same receptacle device as source and delivered to specific receptacle devices as destinations being automatically replaced with a transfer step in accordance with which the sum of the specific transfer volumes of liquid is supposed to be received from the source on a single occasion and the respective specific transfer volume of liquid is supposed to be delivered to the respective destination.

In a further preferred embodiment, the control device combines transfer steps by virtue of transfer steps in accordance with which a specific transfer volume of liquid is supposed to be received from specific receptacle devices as sources and delivered to a further receptacle device as the same destination being automatically replaced with a transfer step in accordance with which the respective specific transfer volume of liquid is supposed to be received from the respective source in immediate succession and the sum of the specific transfer volumes of liquid is supposed to be delivered to the destination on a single occasion.

In a further preferred embodiment, the control device controls the pipetting apparatus and the actuator such that a change of tip of the pipetting apparatus is performed:
immediately after a combined transfer step and/or
after a transfer step with one liquid and before a subsequent transfer step with a different liquid.

It is preferred if, before or after the analysis of the transfer steps, transfer steps are excluded from the analysis of the control device, or multiple different liquids are selected as needing to be mixed for the analysis of the transfer steps, in the configuration interface by means of the input device.

Advantageously, a tip of the pipetting apparatus that has already been used and is contaminated by different types of liquid is reused, in particular for repeat use for at least one further transfer step.

Preferably, the display device displays the altered order of the transfer steps and/or a changed transfer volume in the configuration interface and/or displays the sequence of the transfer steps in a further configuration interface.

A further, also independently realizable, aspect of the present invention relates to a computer-readable storage medium storing a program for carrying out the method according to the present invention. A computer-readable storage medium is in particular a memory stick, a memory card, a flash memory, a CD, a DVD, a Blu-Ray or another storage medium such as a hard disk of a server, from which the program for carrying out the method according to the present invention can be retrievable.

A further, also independently realizable, aspect of the present invention relates to a computer program product having program code means that are designed to carry out the method according to the present invention when the program code means are executed on a computer or by a processor. A computer program product is in particular a file or a data stream providable for retrieval and storage, in particular on online portals or via the Internet.

Further advantages, features, properties and aspects of the present invention will be apparent from the detailed description that follows with reference to the accompanying drawings.

DETAILED DESCRIPTION OF THE INVENTION

In the figures, the same reference signs are used for identical or similar parts or elements, with identical or similar properties being able to be achieved even if a repeat description is not provided.

Figure 1:
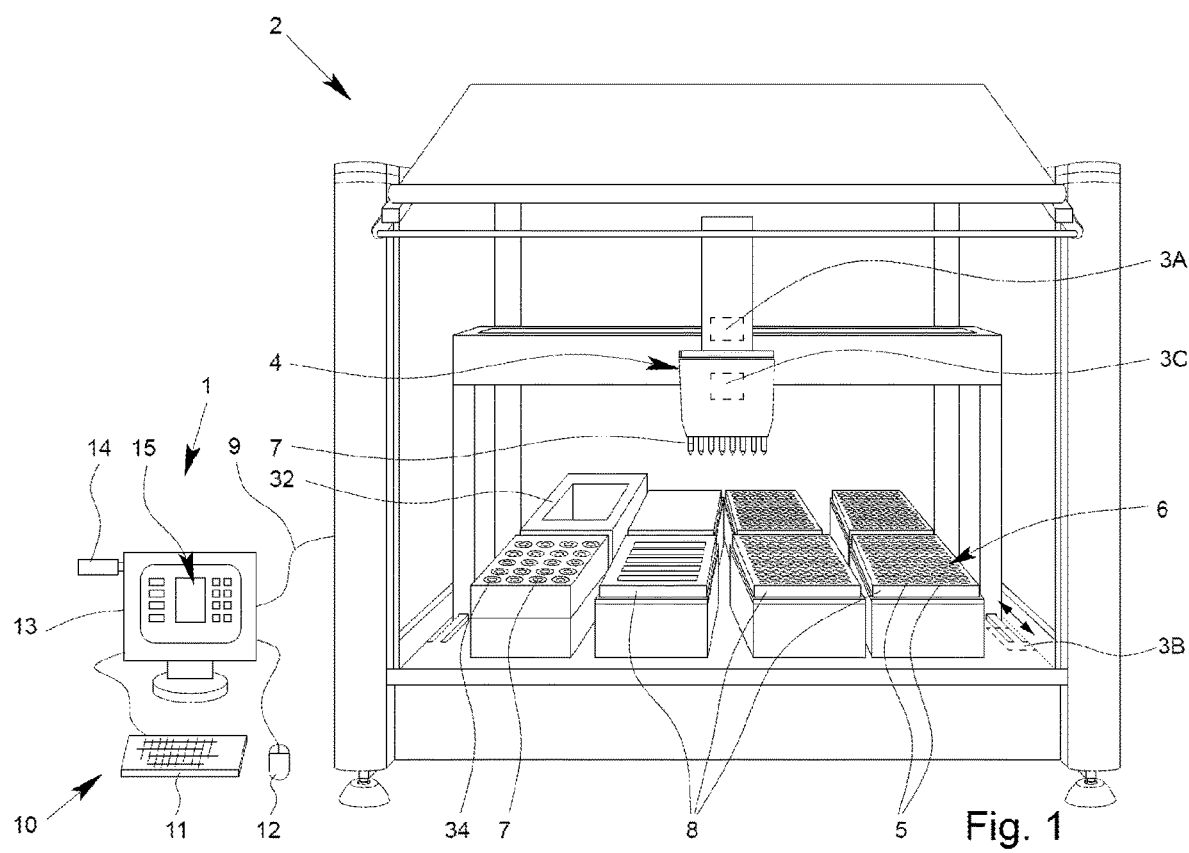
FIG. 1 is a schematic perspective view of an automated pipetting system according to the present invention with a control device according to the present invention.

FIG. 1 shows a schematic depiction of a control device 1 according to the present invention for controlling an automated pipetting system 2. The control device 1 is designed to control at least one actuator 3A, 3B or 3C of the automated pipetting system 2.

The control device 1 is designed to move one or more of the actuators 3A, 3B, 3C of a pipetting apparatus 4 between receptacle devices 5 for liquids 6 that are to be pipetted. Alternatively or additionally, there is provision for the control device 1 to be able to control one or more of the actuators 3A, 3B, 3C such that liquids 6 to be pipetted can be received or delivered by means of the pipetting apparatus 4.

In the depicted example, the actuators 3A, 3B form a positioning device for changing the position of the pipetting apparatus 4, preferably in all three spatial directions. The actuator 3C is preferably in the form of a drive for a cylinder-piston unit for aspirating and delivering liquid. There are also alternative variants for this, however.

The pipetting apparatus 4 in the depicted example is a multichannel pipetting apparatus that preferably has multiple pipette tips 7 or is designed to take liquid 6 from multiple, adjoining receptacle devices 5 or to deliver liquid to adjoining receptacle devices 5. The pipetting apparatus 4 can also be a single-channel pipetting apparatus 4, however, for which there is provision for only one pipette tip 7.

The automated pipetting system 2 can be designed so that the pipetting apparatus 4 is interchangeable, in particular for changing between a single-channel pipetting apparatus 4 and a multichannel pipetting apparatus 4.

The pipetting apparatus 4 preferably has the actuator 3C and is therefore, or by other means, designed to receive liquid 6 in the pipette tip(s) 7 or to deliver liquid therefrom.

This is achieved in particular by the aforementioned cylinder-piston unit or another displacement mechanism, which can be drivable by the actuator 3C.

The control device 1 is designed to control the pipetting apparatus 4 such that a specific transfer volume of liquid 6 is receivable in the pipette tip(s) 7 from at least one of the receptacle devices 5, and at least a portion of the transfer volume of liquid 6 is deliverable to at least one other of the receptacle devices 5 from the pipette tip(s) 7, by means of the pipetting apparatus 4 in a transfer step.

The automated pipetting system 2 preferably has one or more pipetting units 8 that each have multiple receptacle devices 5. The pipetting units 8 are preferably arrangeable at prescribed positions in the automated pipetting system 2. Preferably, receptacles, holders or position markers are provided for this purpose. Further, the pipetting units 8 can optionally be provided with, in particular different, spacers in order to adjust a distance of the receptacle devices 5 from the pipetting apparatus 4 or the pipette tip(s) 7.

The pipetting units 8 are in particular what are known as microtitre plates, PCR plates, deep-well plates and/or slides. The receptacle devices 5 are particularly preferably in the form of vessels, containers, cavities, recesses or the like, in particular for receiving liquids or with a volume in the microlitre range. Alternatively or additionally, however, the receptacle devices 5 can also be surface sections for depositing a drop that are preferably identified accordingly or have a surface coating or pattern that is different from the regions surrounding the respective receptacle device 5.

The control device 1 is preferably connected to the automated pipetting system 2 via a data interface 9. In this way, the control device 1 can communicate with the automated pipetting system 2, can retrieve sensor data from the automated pipetting system 2 or receive sensor data from the automated pipetting system 2 and/or can transmit control signals, in particular for controlling one or more of the actuators 3A, 3B, 3C, to the automated pipetting system 2.

The control device 1 preferably has one or more input devices 10, in particular a keyboard 11 and/or computer mouse 12. Further, the control device 1 preferably has a display device 13, in particular a display or touch display. The sensor of a touch display can act as input device 10 as an alternative or in addition to the keyboard 11 and the computer mouse 12.

The control device 1 preferably has a computer readable storage medium 14 that can store a program for controlling the automated pipetting system 2. The control device 1 can also be connected to a server, however, in particular via the Internet, wherein a computer program product having program code means designed to control the automated pipetting system 2 is retrievable or remotely executable, in particular as what is known as a client-server application. Further, the control device 1 preferably has a processor or controller in order to execute a program for controlling the automated pipetting system 2.

The control device 1 is preferably designed to generate one or more configuration interfaces 15 and/or to present it/them by means of the display device 13. The configuration interfaces 15 are preferably designed and set up to configure, or render configurable, control of the automated pipetting system 2 by means of the control device 1. The control device 1 is particularly preferably designed to generate one or more different configuration interfaces 15, which is discussed in detail in the figures that follow.

Figure 2:
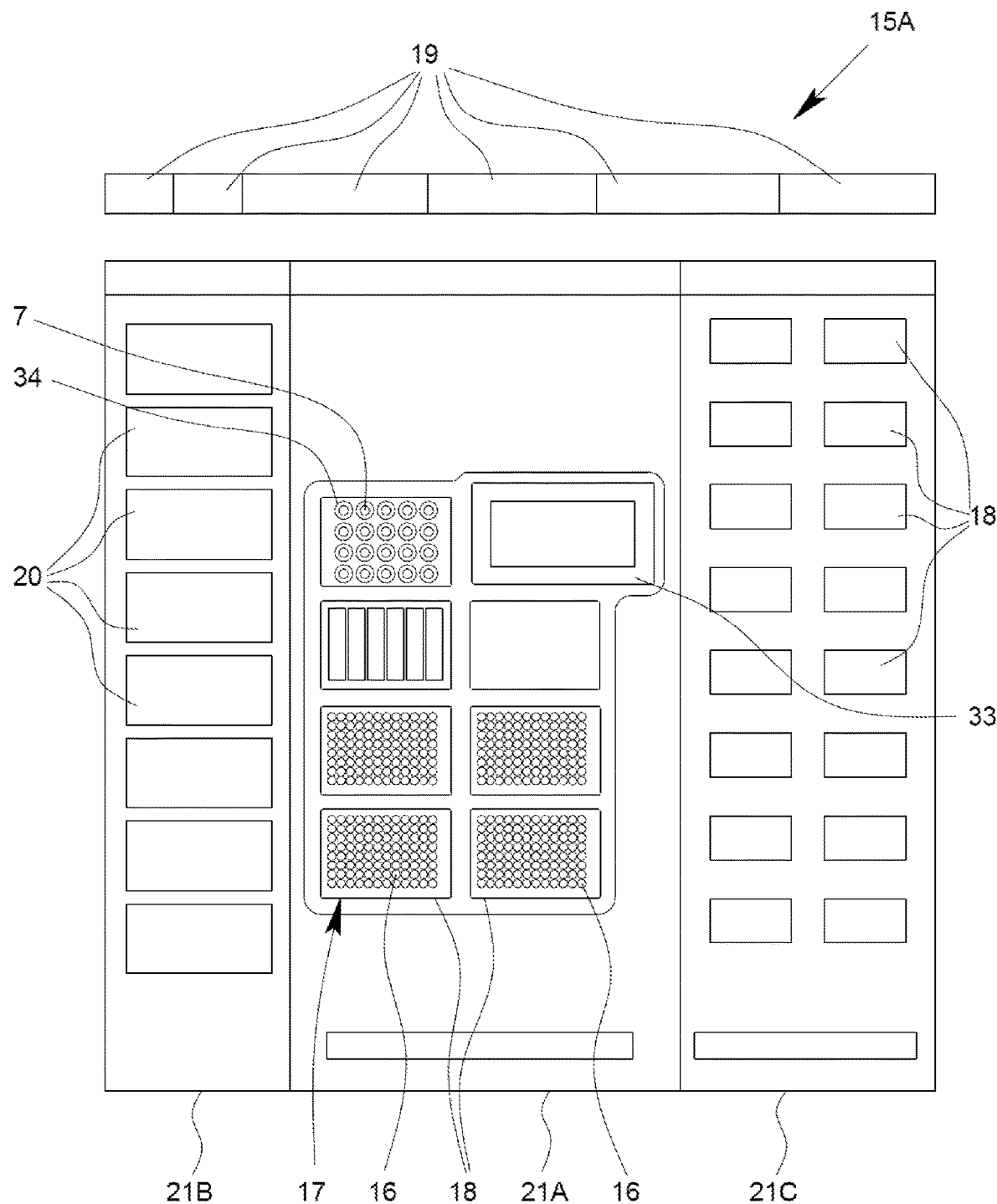
FIG. 2 is a schematic plan view of a first configuration interface of the control device according to the present invention.

FIG. 2 shows a schematic depiction of a first configuration interface 15A of the control device 1 according to the present invention. Multiple wells 16 are graphically depicted in the configuration interface 15A.

The wells 16 each represent and correspond to receptacle devices 5 that are arranged or arrangeable in the automated pipetting system 2. In particular, there is provision for the wells 16 to reflect or represent the arrangement of the receptacle devices 5 in the automated pipetting system 2. To this end, there can be provision for the wells 16 each to be schematic depictions of the receptacle devices 5 or to be otherwise suitable for representing or identifying a receptacle device 5 and, preferably, the position of the receptacle device 5 in relation to the other receptacle devices 5.

There is preferably provision in the configuration interface 15A for wells 16 to be selectable for different virtual positions 17 by means of control using the input device 10, the position or orientation and/or property of the wells 16 corresponding to those of the receptacle devices 5 provided in the automated pipetting system 2.

Particularly preferably, in a manner corresponding to pipetting units 8, multiple wells 16 are each combined to produce graphical pipetting unit equivalents 18, in particular in the form of a graphical representation of a plate, microtitre plate, PCR plate, deep-well plate and/or a plate with slides. The pipetting unit equivalents 18 preferably correspond to pipetting units 8 that are arranged or arrangeable in the automated pipetting system 2. Preferably, pipetting unit equivalents 18 are selectable and/or arrangeable at one or more of the virtual positions 17 in the first configuration interface 15A.

There can be provision for positioning of receptacle devices 5 or pipetting units 8 in the automated pipetting system 2 to result in applicable wells 16 or pipetting unit equivalents 18 being automatically provided or arranged at the applicable virtual positions 17. To this end, the automated pipetting system 2 can have one or more sensors and use the data interface 9 to transmit applicable information or to provide applicable information for retrieval, so that the control device 1 adapts the configuration interface 15A fully automatically. Pipetting unit equivalents 18 or wells 16 can also be positioned at virtual positions 17 on the configuration interface 15A manually or in another way, however.

FIG. 2 also graphically depicts a waste bin 32 for pipette tips 7 by means of a waste bin equivalent 33, pipette tip holders 34 by means of pipette tip holder equivalents 35 and pipette tips 7 intended for installation on the pipetting apparatus 4 by means of pipette tip equivalents 36.

Figure 3:
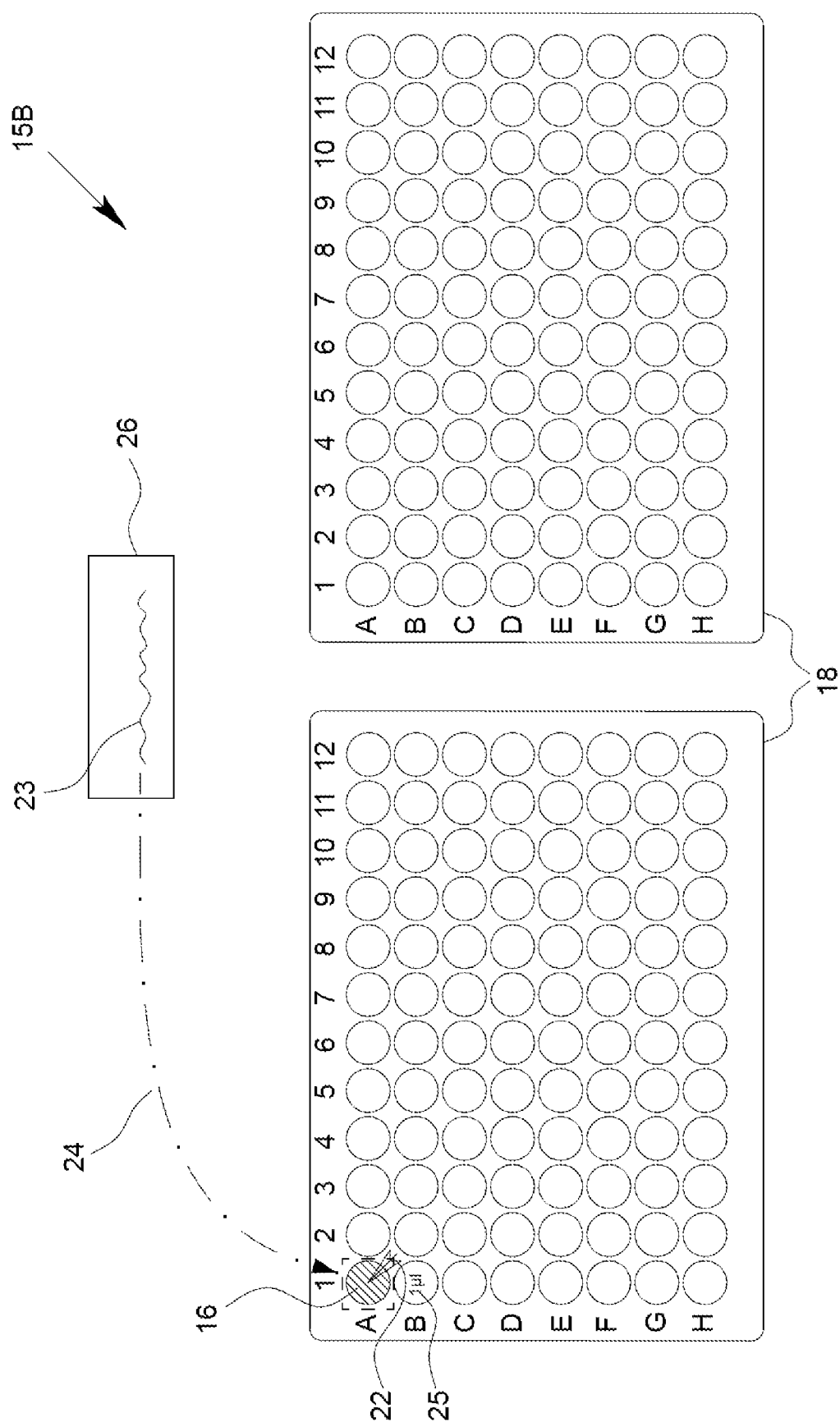
FIG. 3 is a schematic plan view of a second configuration interface of the control device according to the present invention.

The configuration interface 15A is preferably designed to be switchable between different functions, by virtue of changeover means 19. In particular, there is provision for the control device 1 to respond to an input using the input device 10 by activating one of the changeover means 19 in order to change or adapt the configuration interface 15A such that the wells 16 and/or pipetting unit equivalents 18 arranged at the virtual positions 17 are preselectable or selectable in order to subsequently allow a configuration in detail, also called configuration or setup mode. Such a configuration or setup mode is depicted in FIG. 3, for example.

Alternatively or additionally, the configuration interface 15A can be switched to a programming mode, a simulation mode and/or an execution mode, wherein basic functions or pipetting apparatus 4 that are used can be adjustable in the programming mode, the configuration interface 15A is designed to present the sequence and/or the result of control of the automated pipetting system 2 in the simulation mode and/or wherein the automated pipetting system 2 is controlled in a previously configured manner using the control device 1 in the execution mode.

The configuration interface 15A is preferably furthermore designed to use configuration displays 20 to display envisaged occupancies of the virtual positions 17 and optionally additional information in this regard. This advantageously allows transparent configuration and monitoring.

The first configuration interface 15A preferably has multiple display sections 21A, 21B and 21C. In a first display section 21A, there is preferably provision for the pipetting unit equivalents 18 and/or the wells 16. The first display section 21A is preferably provided centrally and/or is not altered by operation of the changeover means 19, which can be provided at the upper edge.

A second display section 21B, in particular arranged on one side of the display section 21A, can have the configuration displays 20. These are schematic depictions of the display section 21A with highlighted virtual positions 17 and/or descriptions of the wells 16 or pipetting unit equivalents 18 arranged at the respective highlighted virtual position 17.

Furthermore, there can be provision in a third display section 21C, which can be provided on a side of the display section 21A that is remote from the display section 21B, in particular, for a configuration menu for adjusting various parameters, functions and/or for selecting one or more of the wells 16 or pipetting unit equivalents 18. Various pipetting unit equivalents 18 and/or wells 16 are preferably selectable in the display section 21C in the setup mode, which allows them to be assigned to the virtual positions 17.

There can alternatively or additionally also be provision for separate configuration interfaces 15A for the individual modes of the configuration interface 15A, the changeover means 19 and/or the display section 21A each preferably being adopted at least substantially identically in the respective configuration interfaces 15A.

In a programming mode of the first configuration interface 15A, which programming mode can be activable via the changeover means 19, it is possible for already chosen or configured method steps or configurations to be displayable, in particular in a chronological order, in the second display section 21B. In the third display section 21C, commands, method steps or instructions are preferably selectable.

In an optional simulation mode of the first configuration interface 15A, which simulation mode can be activable via the changeover means 19, it is possible for a configured sequence to be simulated in the configuration interface 15A and/or with the automated pipetting system 2, in particular by means of appropriate movements of the pipetting apparatus 4.

In an execution mode, which can be activable via the changeover means 19, there is preferably provision in the second display section 21B or third display section 21C for a control panel by means of which the control device 1 is controllable such that the automated pipetting system 2 is controllable by the control device 1 in the previously set-up or configured manner.

FIGS. 3 to 13 are used to explain various further configuration interfaces 15B to 15E or a configuration interface 15D to 15E in different variants or states or with different operating concepts in more detail below.

Preferably, the control device 1 is designed to select one or more of the wells 16 or pipetting unit equivalents 18 in the configuration interface 15A in order to allow one or more of the configuration interfaces 15B to 15E to be opened or generated. In particular, one or more of the wells 16 or pipetting unit equivalents 18 is/are selected or marked in the display section 21A, and operation, in particular operation of a soft switch, of the configuration interface 15A then results in one or more of the configuration interfaces 15B to 15E being generated or displayed. Other solutions are also possible for this, however.

The variants or configuration interfaces 15B to 15E and the associated operation or operability of the control device 1 or of the automated pipetting system 2 can also represent or be separate, combinable, also independently realizable, aspects of the invention.

Configuration interfaces 15B to 15E are presented below in association with FIGS. 3 to 13, the configuration interfaces being designed to configure or specify one or more transfer steps or being used to describe transfer steps, in particular by means of a chronological sequence of the steps, which are described later on in association with the side denoted by 1st and the side denoted by 2nd. These steps, approaches and the like are alternatively or additionally also individually realizable and combinable, however.

FIG. 3 shows a schematic depiction of a second configuration interface 15B of the control device 1 according to the present invention, in which there is provision, in exemplary fashion, for two pipetting unit equivalents 18 having a multiplicity of wells 16. The wells 16 are arranged inside the pipetting unit equivalents 18 at least substantially in the manner of a grid or systematically in another way. Preferably, the wells 16 are each arranged in the manner of a grid in rows and columns, the rows and columns each being denoted such that each individual well 16 is addressable or identifiable in the manner of coordinates by indicating a row and a column.

In the configuration interface 15B from FIG. 3, two different or identical pipetting unit equivalents 18 are arranged next to one another. As a departure from this, however, it is also possible for there to be provision for just one pipetting unit equivalent 18, more than two pipetting unit equivalents 18 or one or more wells 16 independently of pipetting unit equivalents 18 too, preferably corresponding to the occupancy of one or more virtual positions 17.

It is in particular possible for there to be provision for a specific pipetting unit equivalent 18 two or more times in the configuration interface 15B, in particular next to one another, in order to configure transfer steps between receptacle devices 16 of the same pipetting unit 8 in a transparent manner.

One or more wells 16 is or are selectable in the configuration interface 15B, in particular using a selection tool 22, for example a cursor.

By selecting the well(s) 16, it/they can preferably be assigned at least one transfer parameter 23, indicated by the arrow 24 in FIG. 3. The arrow 24 is used merely for explanation and is not part of the configuration interface 15B.

The control device 1 can have a database that can be used to file or store an associated transfer parameter 23 for the different wells 16, in particular by means of the selection or assignment. The database can be a table or other data structure.

Preferably, each well 16 alternatively or additionally has an assigned actual volume parameter 25 representing a liquid volume that is already contained in the respective receptacle device 5 that corresponds to the respective well 16 and/or is ultimately supposed to be present after performance of one or more transfer step(s). The actual volume parameter 25 can be assigned to the respective well 16 in the configuration interface 15B, in particular depicted or depictable in association therewith or within the respective well 16.

The transfer parameter 23 preferably corresponds to a transfer volume, that is to say to a volume of liquid 6 that is supposed to be taken from or delivered to the respective receptacle device 5.

The control device 1 is preferably designed to generate control commands corresponding to the transfer parameters 23, in particular taking into consideration or in the order of their allocation, for controlling the automated pipetting system 2 and, preferably, to transmit them to the automated pipetting system 2 via the data interface 9. As a result, the control device 1 achieves control of the automated pipetting system 2 such that reception of the transfer volume from or delivery of the transfer volume to the respective receptacle device 5 is achieved. This is effected in particular by actuating one or more of the actuators 3A, 3B, 3C of the automated pipetting system 2.

According to an, also independently realizable, aspect of the present invention, there is provision for the control device 1 or the configuration interface 15B to be designed such that the transfer parameter 23 is adjustable or prescribable in or using the configuration interface 15B. In particular, the configuration interface 15B has an input mask 26 or a menu, a selection box or the like in which the transfer parameter 23 can be input, selected, changed or otherwise prescribed, in particular by means of the keyboard 11.

The transfer parameter 23 is preferably adjustable on the same configuration interface 15B on which individual wells 16 are also selectable and the transfer parameter 23 is assignable thereto. This has been found to be particularly advantageous for fast configuration and transparent operation of the automated pipetting system 2 using the control device 1.

The transfer parameter 23 is or particularly preferably corresponds to the transfer volume, that is to say to a liquid volume of liquid 6 that is supposed to be received or delivered by the pipetting apparatus 4 with the pipette tip(s) 7.

Alternatively or additionally, the transfer parameter 23 can also have or correspond to a quantity of transfer material, in particular in mol, a transfer tool, in particular a single-channel or multi-channel pipetting apparatus 4, a transfer pattern and/or a transfer or target concentration. Particularly preferably, however, the transfer parameter 23 corresponds to a respective transfer volume that can be determinable or calculable from the amount of transfer material, the transfer or target concentration.

Figure 4:
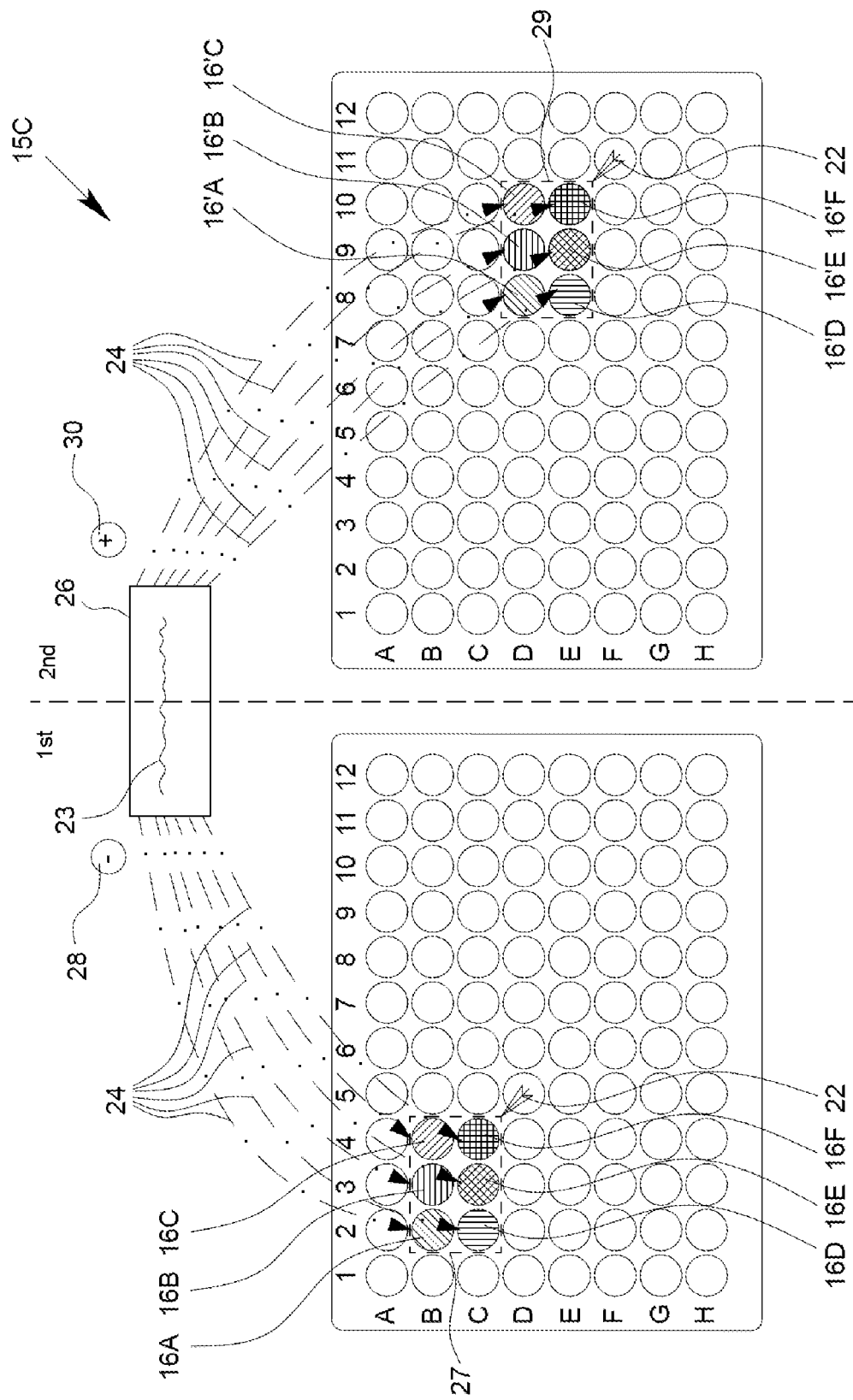
FIG. 4 is a schematic plan view of a third configuration interface of the control device according to the present invention.

FIG. 4 shows a schematic depiction of a third configuration interface 15C of the control device 1 according to the present invention.

For fundamental aspects, in particular relating to the assignment of the transfer parameter 23, explicit reference is made at this juncture to the explanations in association with FIG. 3. Only further special features of more complex control procedures are therefore discussed below, the properties and features described in association with FIG. 3 preferably being fundamental or applicable as appropriate. The same applies to the further configuration interfaces 15D to 15E, which are explained in association with FIGS. 5 to 13.

The configuration interface 15C from FIG. 4 is divided into a first and a second section by a dashed line for reasons of better comprehension, this dashed line and the numbers 1st and 2nd not being part of the configuration interface 15C but rather merely being supposed to depict a preferred chronological order. Accordingly, the arrows 24 are likewise merely depicted for explanatory purposes, but are preferably not shown in the respective configuration interface 15 and not part thereof.

In the configuration interface 15C, a well 16 or a first group 27 of wells 16A to 16F, highlighted here by a dashed border, is preferably selected on the 1st side. By selecting the wells 16A to 16F, these wells 16A to 16F are preferably assigned the transfer parameter(s) 23, as indicated by the arrows 24.

The respective transfer parameter 23 respectively assigned in this first step is preferably a transfer parameter 23 that corresponds to one or more transfer volumes to be taken, as indicated by the minus symbol 28 in the configuration interface 15C, this being used merely for explanatory purposes and preferably not being part of the configuration interface 15C or being displayable by means of the control device 1.

Following selection of a first well 16A to 16F or multiple first wells 16A to 16F as a first group 27 on the 1st side, a second selection of a second well 16'A to 16'F or a selection of a second group 29 of second wells 16'A to 16'F can subsequently be made on the 2nd side. This selection preferably results in transfer parameters 23 corresponding to one or more transfer volumes to be delivered being assigned to the respective second wells 16'A to 16'F. In the configuration interface 15C, this time sequence is symbolized by the central dashed line and the denotation by 1st and 2nd.

It is preferred for a first selection of a first well 16A to 16F or of a first group 27 of first wells 16A to 16F made on the 1st side to result in every selected first well 16A to 16F being automatically assigned a transfer parameter 23 corresponding to a transfer volume to be taken. If this first selection is followed by a second selection, made on the 2nd side, of a second well 16'A to 16'F or a group 29 of second wells 16'A to 16'F, it is preferred if every selected second well 16'A to 16'F is automatically assigned a transfer parameter 23 corresponding to a transfer volume to be delivered.

The first wells 16A to 16F, which are assigned a transfer parameter 23 corresponding to a transfer volume to be taken, as also indicated by the minus symbol 28, are also called source wells. Second wells 16'A to 16'F, which are assigned a transfer parameter 23 corresponding to a transfer volume to be delivered, are preferably also referred to as destination wells. A selection of wells 16 on the 1st side thus preferably automatically results in the definition of source wells 16A to 16F, while a selection of wells 16 on the 2nd side results in the definition of destination wells 16'A to 16'F.

The receptacle devices 5 from which liquid 6 to be pipetted is supposed to be received by the pipetting apparatus 4 correspond to the source wells 16A to 16F. The receptacle devices 5 to which liquid 6 to be pipetted is supposed to be delivered by the pipetting apparatus 4 correspond to the destination wells 16'A to 16'F.

Multiple source wells 16A to 16F and multiple destination wells 16'A to 16'F are selectable in the configuration interface 15C by means of the input device 10. The control device 1 is designed such that, to specify multiple transfer steps and the order of execution thereof by the pipetting apparatus 4 and the actuator 3, multiple previously selected source wells 16A to 16F are assignable to multiple destination wells 16'A to 16'F in the configuration interface 15C by selecting these destination wells 16'A to 16'F.

When a group 27 of first wells 16A to 16F is selected on the 1st side and a group 29 of second wells 16'A to 16'F is subsequently selected on the 2nd side, a paired 1:1 association is preferably automatically made. When using a multichannel pipetting apparatus 4 corresponding to the groups 27, 29, this 1:1 association is automatically achieved or made possible by separate pipette tips 7. When groups 27, 29 that do not correspond to a multichannel pipetting apparatus 4 are selected, selection of the groups 27, 29 is followed by associations or transfer processes being automatically split, so that the control results in single transfers taking place or individual selections, which each change between the group 27 of first wells 16A to 16F and the group 29 of second wells 16'A to 16'F, being fabricated or the effect of a respective paired association being made being achieved otherwise.

In the depicted example, the control device 1 is designed and set up to take the number of pipette tips 7 of the respectively chosen pipetting apparatus 4 as a basis for controlling the automated pipetting system 2 following selection of two groups 27, 29 such that liquid 6 is gradually transferred in successive processes from the receptacle devices 5 corresponding to the first wells 16A to 16F to each of the receptacle devices 5 corresponding to the second wells 16'A to 16'F.

In the configuration interface 15C, mutually assigned or mutually corresponding wells 16 are preferably denoted as associated or identical with one another. In the depicted example, mutually associated or corresponding wells 16 have the same shading. Alternatively or additionally, the same or identical colors or other markings can also be used, however.

Preferably, a context menu is generable or activable in the configuration interface 15C, in particular by selecting or alternatively selecting the first group 27 or the source wells 16A to 16F. The context menu preferably has one or more options for virtually modifying the structure or arrangement and/or number of selected source wells 16A to 16F of the group 27 for a subsequent or further selection of destination wells 16'A to 16'F. The modification is virtual insofar as the selected source wells 16A to 16F themselves are not modified but rather a transfer pattern (that is to say a graphical representation) is generated and this is modified.

Selection of the source wells 16A to 16F results in a graphical representation of the selected source wells 16A to 16F being presented. The graphical representation can then be altered in respect of number and arrangement of the wells by means of the options of the context menu. Finally, the graphical representation can be used to simultaneously (that is to say synchronously, all at once) select multiple destination wells 16'A to 16'F as a second group 29 on the 2nd side. The selection results in the selected source wells 16A to 16F being simultaneously assigned to the destination wells 16'A to 16'F.

The selected source wells 16A to 16F are therefore simultaneously (all at once) assignable to multiple destination wells 16'A to 16'F such that the arrangement and/or number of assigned destination wells 16'A to 16'F differs from the arrangement and/or number of selected source wells 16A to 16F. This results in the selected source wells 16A to 16F and their assigned destination wells 16'A to 16'F being assigned transfer parameters 23 such that the respective corresponding transfer volume is transferable from the receptacle devices 5 corresponding to the selected source wells 16'A to 16'C to the receptacle devices 5 corresponding to the assigned destination wells 16'A to 16'F.

As can be seen in FIG. 4, the assigned destination wells 16'A to 16'F are displayable in the same configuration interface 15C as the selected source wells 16A to 16F.

The control device 1 is preferably designed to control the automated pipetting system 2 such that either a multichannel pipetting apparatus 4 or, in a manner broken down into multiple transfer processes, a single-channel pipetting apparatus 4 is used to effect a 1:1 volume transfer between the individual receptacle devices 5 that correspond firstly to the group 27 or the source wells 16A to 16F and secondly to the group 29 or the destination wells 16'A to 16'F. In particular, liquid 6 is thus received from the receptacle device 5 corresponding to the source well 16A and, following appropriate movement of the pipetting apparatus 4, delivered to the receptacle device 5 corresponding to the destination well 16'A. This is then followed by the same in association with the source well 16B and the destination well 16'B, and so on. In this way, liquid 6 is transferable by means of the control device 1 and the automated pipetting system 2 such that neighborhood conditions and orientations of liquids 6 in the respective receptacle devices 5 are systematically changeable.

Figure 5:
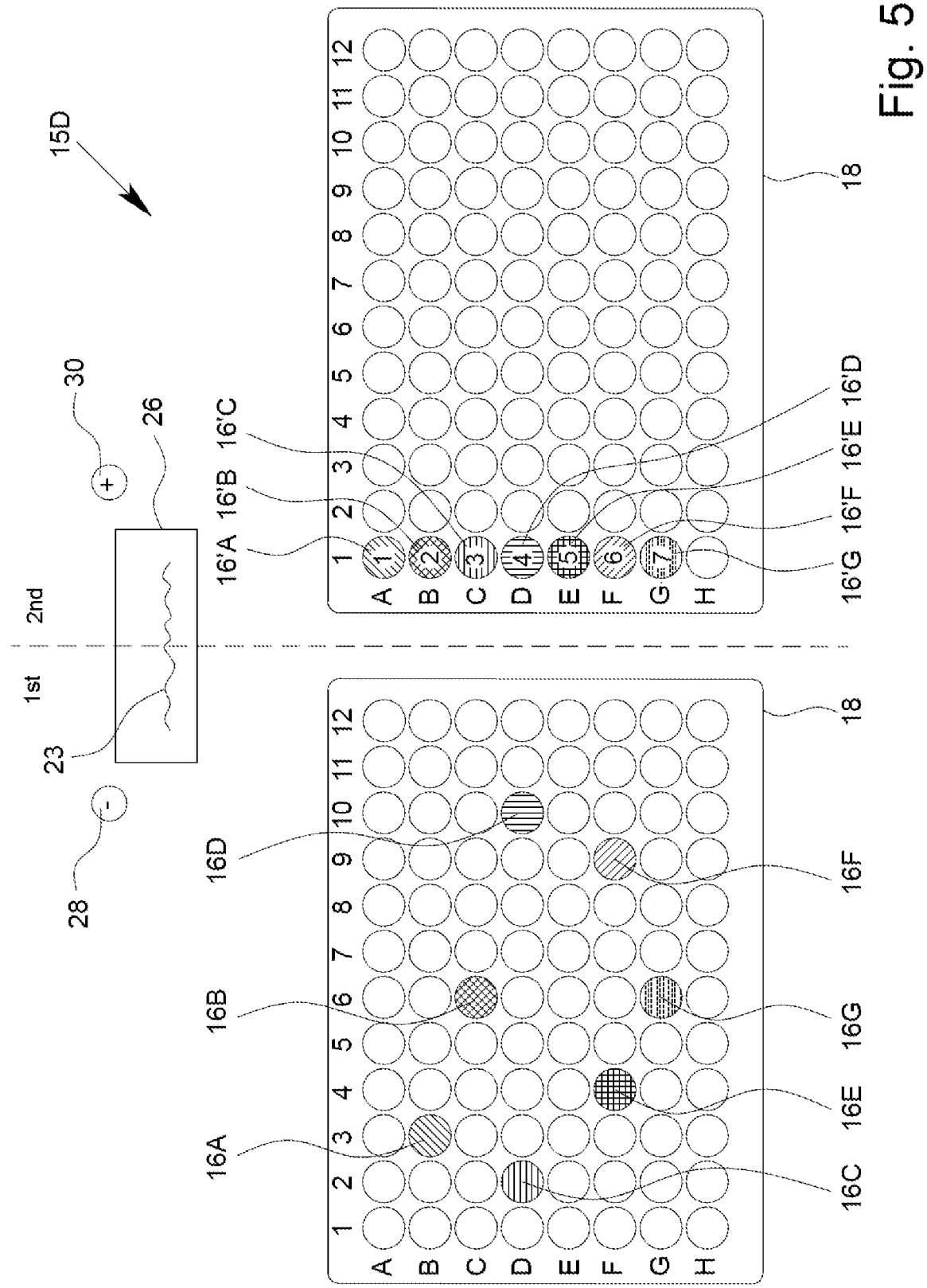
FIG. 5 is a schematic plan view of a fourth configuration interface of the control device according to the present invention in a first state.

FIG. 5 shows a schematic depiction of a first state of a fourth configuration interface 15D of the control device 1 according to the present invention. Multiple unbundled source wells 16A to 16G are selected and presented on the 1st side in the configuration interface 15D. In this context, the term "unbundled" is supposed to be understood to mean that there is at least one unselected well on one of the shortest journeys (oriented to rows and columns) between at least two wells, that is to say that the selection relates to noncontinuously adjoining wells.

Using the context menu or else another method, for which there is preferably provision in the configuration interface 15D, there is the option of it preferably being selectable or selected that the selected, unbundled source wells 16A to 16G are simultaneously assignable to destination wells 16'A to 16'G on the 2nd side such that the destination wells 16'A to 16'G, are arranged in bundled fashion, preferably in columns. Preferably, it is possible to specify in how many columns situated next to one another the destination wells 16'A to 16'G are supposed to be arranged.

In the example depicted in FIG. 5, the unbundled source wells 16A to 16G selected on the 1st side are assigned to the destination wells 16'A to 16'G arranged beneath one another in column 1 on the 2nd side. Here, the column number chosen was thus "1".

This assignment now results in transfer steps being specified. In accordance with a first transfer step, liquid 6 needs to be taken from the receptacle device 5 corresponding to the source well 16A (column 3, row B) and delivered to the receptacle device 5 corresponding to the destination well 16'A (column 1, row A). In accordance with a second transfer step, liquid 6 needs to be taken from the receptacle device 5 corresponding to the source well 16B (column 6, row C) and delivered to the receptacle device 5 corresponding to the destination well 16'B (column 1, row B). The same applies to the remainder of the transfer steps.

The numbers "1" to "7" depicted in the destination wells 16'A to 16'G indicate the order of execution of the transfer steps by the pipetting apparatus 4 and the actuator 3. First, the first specified transfer step is thus executed, followed by the second transfer step, etc.

Figure 6:
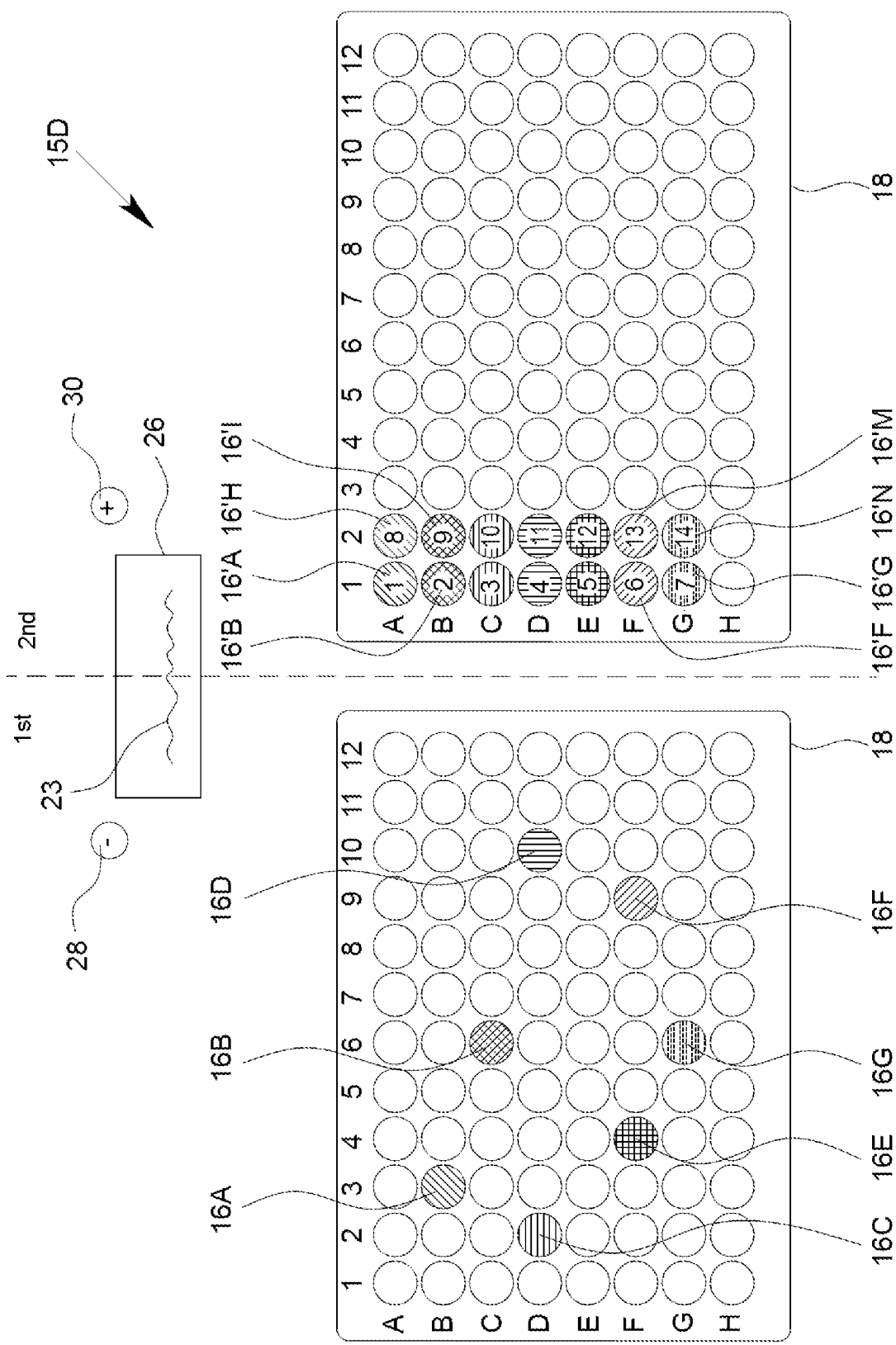
FIG. 6 is a schematic plan view of the fourth configuration interface from FIG. 5 in a second state.

FIG. 6 shows a schematic depiction of a second state of the fourth configuration interface 15D from FIG. 5. In addition to the first to seventh transfer steps shown in FIG. 5, seven further transfer steps are specified for the state depicted in FIG. 6. In comparison with the first to seventh transfer steps, the destination wells are different, the reason being that they are situated not in the first but rather in the second column on the 2nd side. In accordance with the eighth transfer step, liquid 6 thus again needs to be taken from the receptacle device 5 corresponding to the source well 16A (column 3, row B) but delivered to the receptacle device 5 corresponding to the destination well 16'H (column 2, row A). In accordance with the ninth transfer step, liquid 6 needs to be taken from the receptacle device 5 corresponding to the source well 16B (column 6, row C) and delivered to the receptacle device 5 corresponding to the destination well 16'I (column 2, row B). The same applies to the remainder of the transfer steps.

Figure 7:
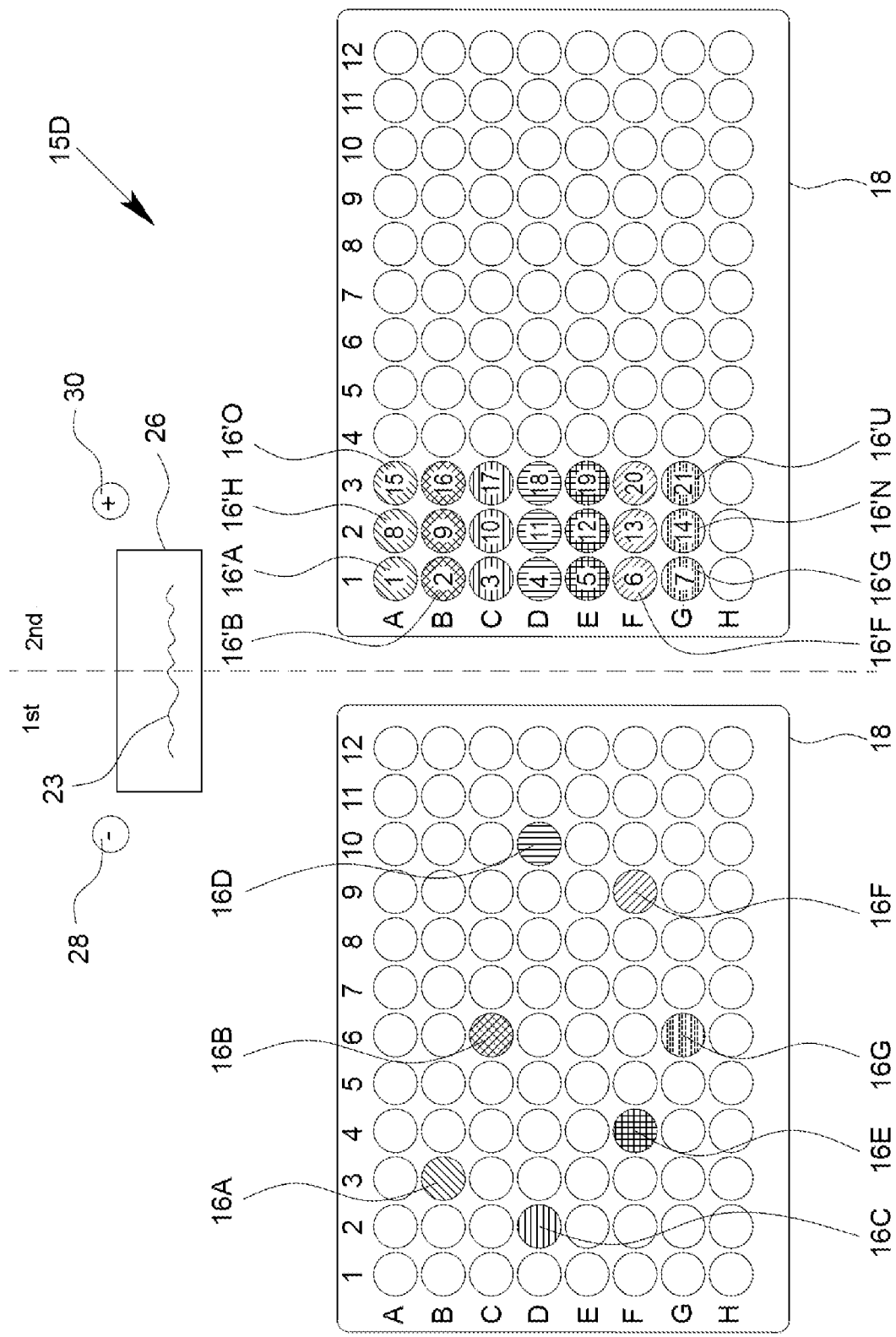
FIG. 7 is a schematic plan view of the fourth configuration interface from FIG. 5 in a third state.

FIG. 7 shows a schematic depiction of a third state of the fourth configuration interface 15D from FIG. 5. In addition to the first to 14th transfer steps shown in FIG. 6, seven further transfer steps are specified for the state depicted in FIG. 7. In comparison with the first to seventh transfer steps, the destination wells are different, the reason being that they are situated not in the first but rather in the third column on the 2nd side. In accordance with the 15th transfer step, liquid 6 thus again needs to be taken from the receptacle device 5 corresponding to the source well 16A (column 3, row B) but delivered to the receptacle device 5 corresponding to the destination well 16'O (column 3, row A). In accordance with the 16th transfer step, liquid 6 needs to be taken from the receptacle device 5 corresponding to the source well 16B (column 6, row C) and delivered to the receptacle device 5 corresponding to the destination well 16'P (column 3, row B). The same applies to the remainder of the transfer steps.

In the preferred exemplary embodiment depicted, the control device 1 is designed to control the pipetting apparatus 4 and the actuator 3 such that a change of pipette tip 7 of the pipetting apparatus 4 is performed after a transfer step with one liquid 6 and before a subsequent transfer step with a different liquid 6.

In the example depicted in FIG. 7, a change of pipette tips 7 would therefore be performed after or upon every transfer step. Overall, there would be 21 changes of pipette tips 7.

The execution of these transfer steps specified in this manner would result in the following sequence: first, the pipetting apparatus 4 is moved to a pipette tip holder 34. There, a pipette tip 7 is mounted on the pipetting apparatus 4. The pipetting apparatus 4 is then moved to the receptacle device 5 that corresponds to the source well 16A. There, the pipetting apparatus 4 will receive the transfer volume defined by means of the transfer parameter 23 from this receptacle device 5. The pipetting apparatus 4 is then moved to the receptacle device 5 that corresponds to the destination well 16'A. There, the pipetting apparatus 4 will deliver the transfer volume defined by means of the transfer parameter 23 to this receptacle device 5. The pipetting apparatus 4 is then moved to the waste bin 32. The used pipette tip 7 is discarded therein. The other transfer steps follow analogously.

It should be taken into consideration that the journeys between a receptacle device 5 that corresponds to source wells and a receptacle device 5 that corresponds to destination wells and also the journeys to the waste bin 32 are longer by a multiple than the journeys between two receptacle devices 5 that correspond to source wells or between two receptacle devices 5 that correspond to destination wells.

Figure 8:
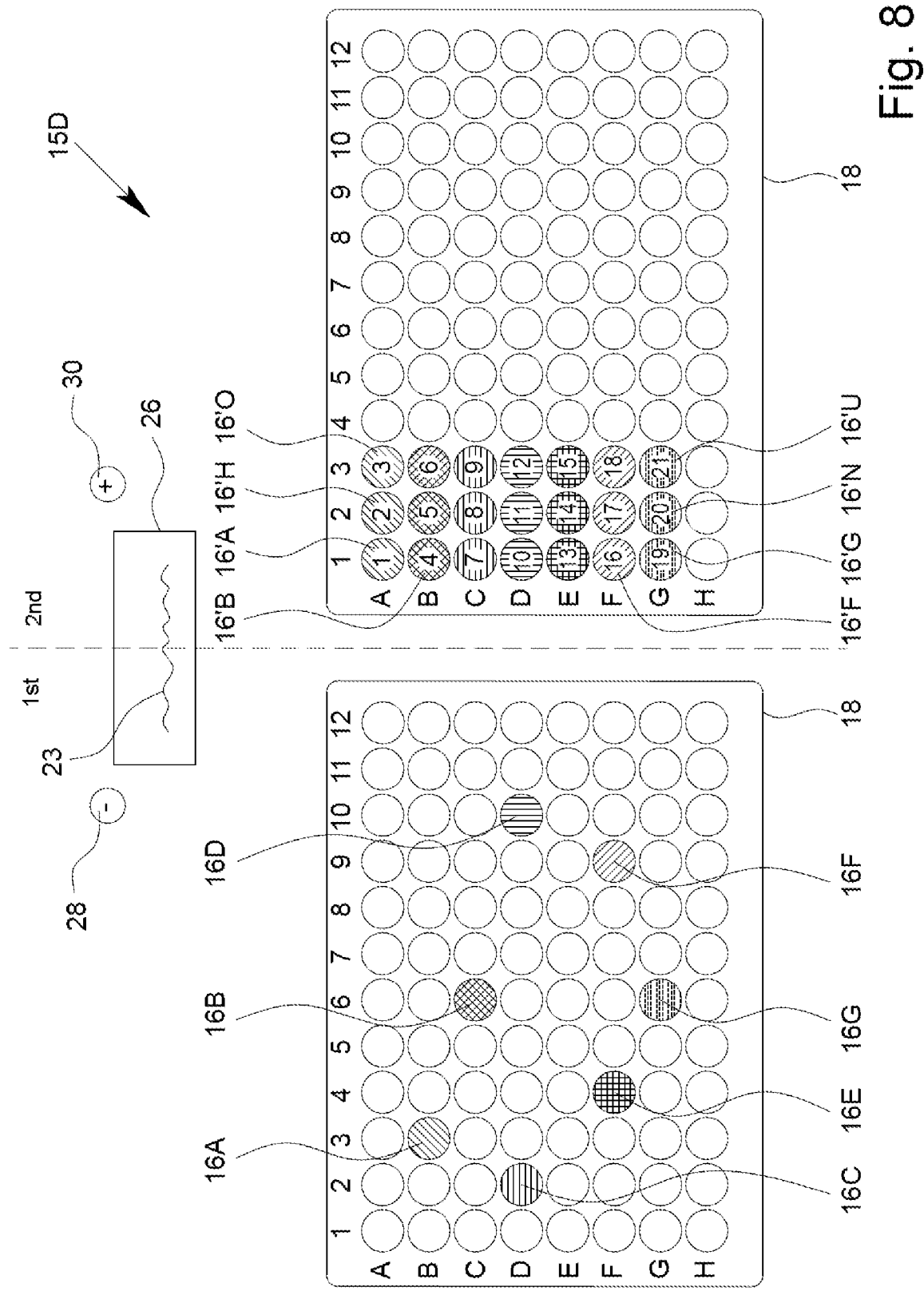
FIG. 8 is a schematic plan view of the fourth configuration interface from FIG. 5 in a fourth state.

FIG. 8 shows a schematic depiction of a fourth state of the fourth configuration interface 15D from FIG. 5. Using the context menu or else another method, for which there is preferably provision in the configuration interface 15D, there is the option of it preferably being selectable or selected that the order of execution of the selected destination wells 16'A to 16'U is automatically altered by the control device 1 such that transfer steps in accordance with which liquid 6 is supposed to be received from the same receptacle device 5 are immediately successive.

The control device 1 is now designed so as, before the execution of the specified transfer steps by the pipetting apparatus 4 and the actuator 3, to analyze the specified order of execution of these transfer steps and the liquid 6 to be pipetted in these transfer steps. In the present exemplary embodiment, the control device 1 looks, during the analyzing, for transfer steps in accordance with which compatible, in particular identical, liquids 6 need to be pipetted. During the analyzing of the transfer steps as shown in FIG. 7, the control device 1 will find that, in accordance with transfer steps 1, 8 and 15, identical liquids 6 need to be pipetted, because the liquids 6 to be pipetted all need to be taken from the receptacle device 5 that corresponds to the source well 16A. This also applies to transfer steps 2, 9, 16 and 3, 10, 17 etc. These transfer steps with identical liquids 6 are depicted using the same shading in FIGS. 7 and 8.

During the analyzing, the specified transfer steps are additionally examined by the control device 1 for whether these transfer steps are independent of other transfer steps or the execution of these transfer steps can take place in a different order from that specified. In the present example, there are no dependencies.

The control device 1 is now designed so as, after the analysis, to automatically alter the order of execution of these analyzed transfer steps, specifically such that transfer steps in accordance with which liquid 6 is supposed to be taken from the same receptacle device 5 are immediately successive. The resultant changed order is depicted in FIG. 8 and discernible from the respective number in the destination wells 16'A to 16'U. E.g. the transfer step previously specified as eighth transfer step now needs to be executed as the second transfer step.

The execution of these transfer steps specified in this manner would result in the following sequence: first, the pipetting apparatus 4 is moved to a pipette tip holder 34. There, a pipette tip 7 is mounted on the pipetting apparatus 4. The pipetting apparatus 4 is then moved to the receptacle device 5 that corresponds to the source well 16A. There, the pipetting apparatus 4 will receive the transfer volume defined by means of the transfer parameter 23 from this receptacle device 5. The pipetting apparatus 4 is then moved to the receptacle device 5 that corresponds to the destination well 16'A. There, the pipetting apparatus 4 will deliver the transfer volume defined by means of the transfer parameter 23 to this receptacle device 5. The pipette tip 7 is now not changed, but rather the pipetting apparatus 4 is moved to the receptacle device 5 that corresponds to the source well 16A. There, the pipetting apparatus 4 will receive the transfer volume defined by means of the transfer parameter 23 from this receptacle device 5. The pipetting apparatus 4 is then moved to the receptacle device 5 that corresponds to the destination well 16'H. There, the pipetting apparatus 4 will deliver the transfer volume defined by means of the transfer parameter 23 to this receptacle device 5. The pipette tip 7 is now again not changed, but rather the pipetting apparatus 4 is again moved to the receptacle device 5 that corresponds to the source well 16A. There, the pipetting apparatus 4 will receive the transfer volume defined by means of the transfer parameter 23 from this receptacle device 5. The pipetting apparatus 4 is then moved to the receptacle device 5 that corresponds to the destination well 16'O. There, the pipetting apparatus 4 will deliver the transfer volume defined by means of the transfer parameter 23 to this receptacle device 5. The pipetting apparatus 4 is then moved to the waste bin 32. The used pipette tip 7 is discarded therein. The other transfer steps 4 to 21 follow analogously.

All in all, only seven instead of 21 changes of pipette tips 7 are performed here, namely after transfer steps 3, 6, 9, 12, 15, 18 and 21. This saves materials (pipette tips 7) and time (for the journeys to the waste bin and back).

The control device 1 here is also designed to automatically alter the order of execution of these transfer steps such that transfer steps in accordance with which liquid 6 is supposed to be delivered to the same receptacle device 5 are immediately successive. Such transfer steps are not specified in the present example, however.

Figure 9:
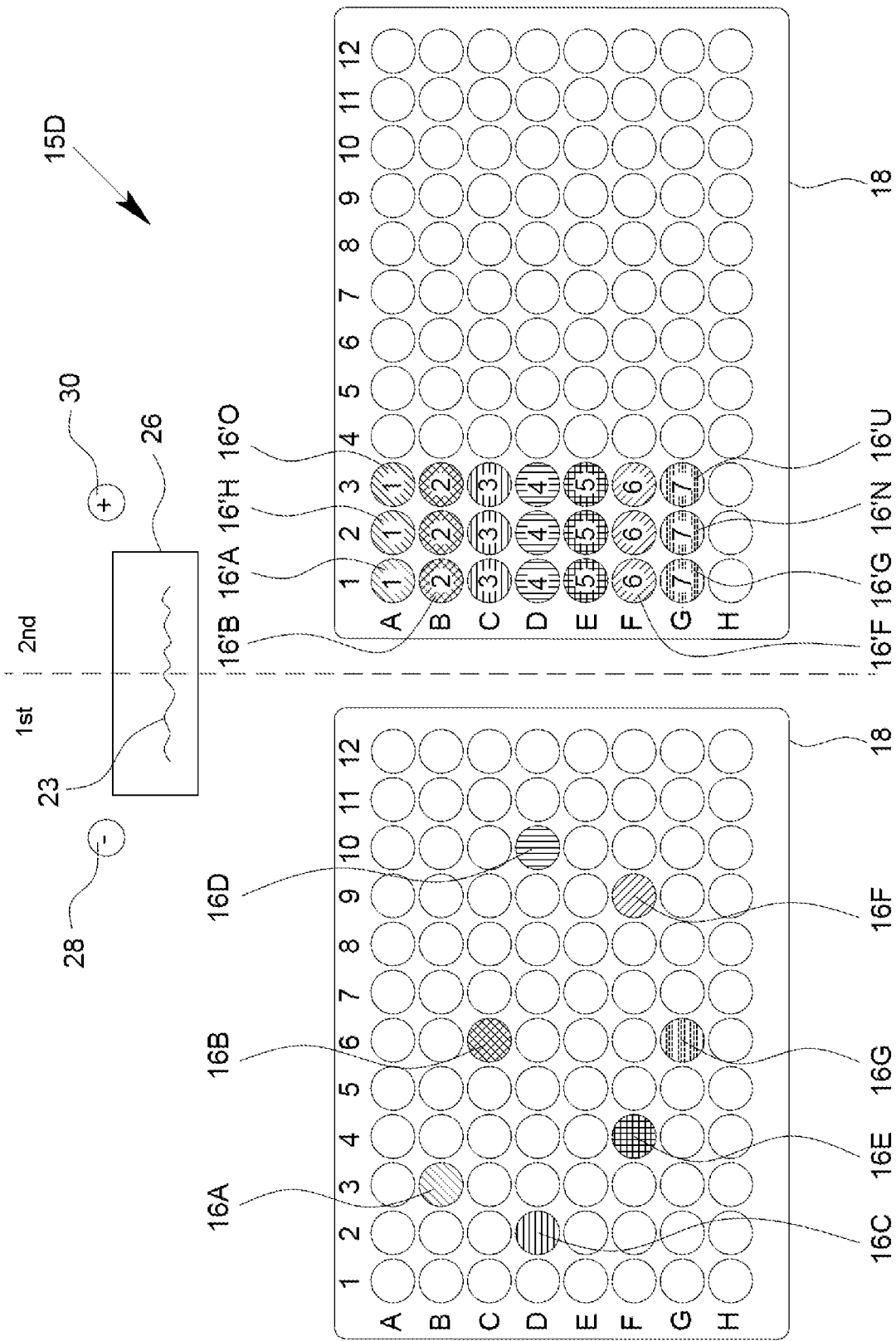
FIG. 9 is a schematic plan view of the fourth configuration interface from FIG. 5 in a fifth state.

FIG. 9 shows a schematic depiction of a fifth state of the fourth configuration interface 15D from FIG. 5. Automatically after the previously explained change of order of the specified transfer steps or using the context menu or else another method, for which there is preferably provision in the configuration interface 15D, there may be provision or a prompt for transfer steps to be combined by the control device 1 by virtue of transfer steps in accordance with which a specific transfer volume of liquid 6 is supposed to be received from the same receptacle device 5 as source and delivered to specific receptacle devices 5 as destinations being automatically replaced with a transfer step in accordance with which the sum of the specific transfer volumes of liquid 6 is supposed to be received from the source 5 on a single occasion and the respective specific transfer volume of liquid 6 is supposed to be delivered to the respective destination 5.

As such, in accordance with transfer steps 1 to 3 from FIG. 8, a specific transfer volume of liquid 6 needs to be received from the receptacle device 5 that corresponds to the source well 16A as source and delivered to the receptacle devices 5 that correspond to the destination wells 16'A, 16'H, 16'O as destinations. The control device 1 automatically replaces these transfer steps 1 to 3 with a new transfer step 1 in accordance with which the sum of the specific transfer volumes of liquid 6 is supposed to be received from the source 5 on a single occasion and the respective specific transfer volume of liquid 6 is supposed to be delivered to the respective destination 5. The same applies to transfer steps 4, 5, 6 and 7, 8, 9 etc.

The execution of these transfer steps combined in this manner would now result in the following sequence: first, the pipetting apparatus 4 is moved to a pipette tip holder 34. There, a pipette tip 7 is mounted on the pipetting apparatus 4. The pipetting apparatus 4 is then moved to the receptacle device 5 that corresponds to the source well 16A. There, the pipetting apparatus 4 will receive the sum of the specific transfer volumes of liquid 6 from this receptacle device 5 on a single occasion. The pipetting apparatus 4 is then moved to the receptacle device 5 that corresponds to the destination well 16'A. There, the pipetting apparatus 4 will deliver the transfer volume defined by means of the transfer parameter 23 to this receptacle device 5. The pipette tip 7 is now not changed, but rather the pipetting apparatus 4 is moved to the receptacle device 5 that corresponds to the destination well 16'H. There, the pipetting apparatus 4 will deliver the transfer volume defined by means of the transfer parameter 23 to this receptacle device 5. The pipette tip 7 is now again not changed, but rather the pipetting apparatus 4 is moved to the receptacle device 5 that corresponds to the destination well 16'O. There, the pipetting apparatus 4 will deliver the transfer volume defined by means of the transfer parameter 23 to this receptacle device 5. The pipetting apparatus 4 is then moved to the waste bin 32. The used pipette tip 7 is discarded therein. The other transfer steps 2 to 7 follow analogously.

All in all, only seven changes of pipette tips 7 are performed here, namely after transfer steps 1 to 7. Additionally, the pipetting apparatus 4 is moved to each source 5 only exactly once. This saves materials (pipette tips 7) and time (for the journeys to the waste bin 32 and back and for the journeys between sources 5 and destinations 5).

The control device 1 here is also designed to automatically combine transfer steps by virtue of transfer steps in accordance with which a specific transfer volume of liquid 6 is supposed to be received from specific receptacle devices 5 as sources and delivered to a further receptacle device 5 as the same destination being automatically replaced with a transfer step in accordance with which the respective specific transfer volume of liquid 6 is supposed to be received from the respective source in immediate succession and the sum of the specific transfer volumes of liquid 6 is supposed to be delivered to the destination on a single occasion. Such transfer steps are not specified in the present example, however.

Preferably, there is provision for, before or after the analysis of the transfer steps, transfer steps to be excludable from the analysis of the control device 1, or multiple different liquids 6 to be selectable as needing to be mixed for the analysis of the transfer steps, in the configuration interface 15D by means of the input device 10.

Figure 10:
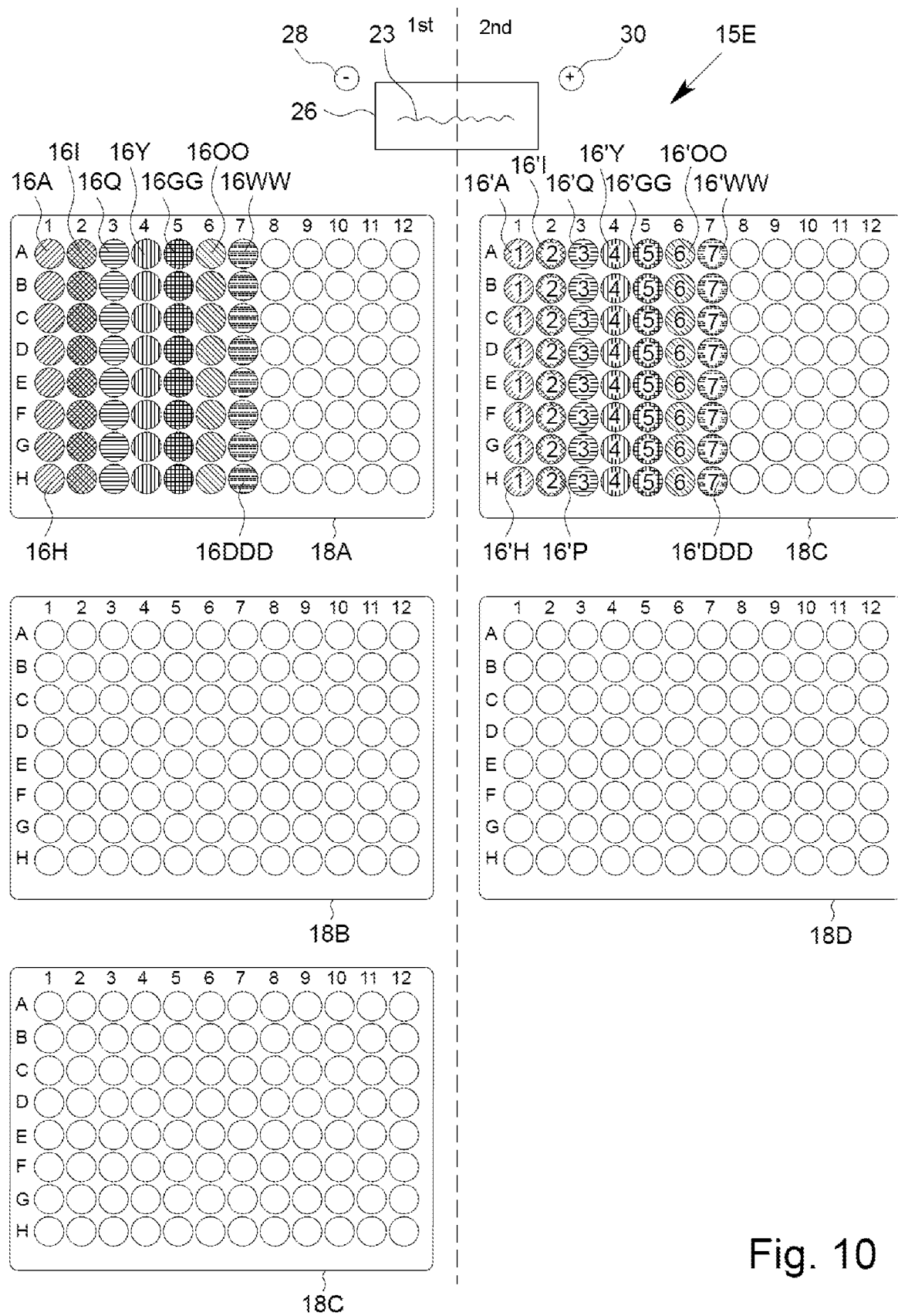
FIG. 10 is a schematic plan view of a fifth configuration interface of the control device according to the present invention in a first state.

FIG. 10 shows a schematic depiction of a first state of a fifth configuration interface 15E of the control device 1 according to the present invention. There is provision in the configuration interface 15E for a multichannel pipetting apparatus for the pipetting apparatus 4, which has eight pipette tips 7 and is designed to take liquid 6 from eight adjoining receptacle devices 5 and to deliver liquid to eight adjoining receptacle devices 5.

In the configuration interface 15E, multiple source wells 16A to 16DDD are selected and presented on the pipetting unit equivalent 18A (as first source plate) on the 1st side and multiple destination wells 16'A to 16'DDD are selected and presented on the pipetting unit equivalent 18C (as first destination plate) on the 2nd side. The same shadings in a column (1 to 7) indicate that in a (first) transfer step the multichannel pipetting apparatus 4 is supposed to be used to simultaneously receive liquids 6 from the receptacle devices 5 that correspond to the source wells 16A to 16H of the pipetting unit equivalent 18A. In this transfer step, the liquids 6 are supposed to be delivered to the receptacle devices 5 that correspond to the destination wells 16'A to 16'H of the pipetting unit equivalent 18C. In a further (second) transfer step, the multichannel pipetting apparatus 4 is supposed to be used to simultaneously receive liquids 6 from the receptacle devices 5 that correspond to the source wells 16I to 16P of the pipetting unit equivalent 18A. In this second transfer step, the liquids 6 are supposed to be delivered to the receptacle devices 5 that correspond to the destination wells 16'I to 16'P of the pipetting unit equivalent 18C. The same applies to the remainder of the transfer steps. The numbers "1" to "7" in the destination wells 16'A to 16'DDD indicate the order of execution of the specified transfer steps.

Figure 11:
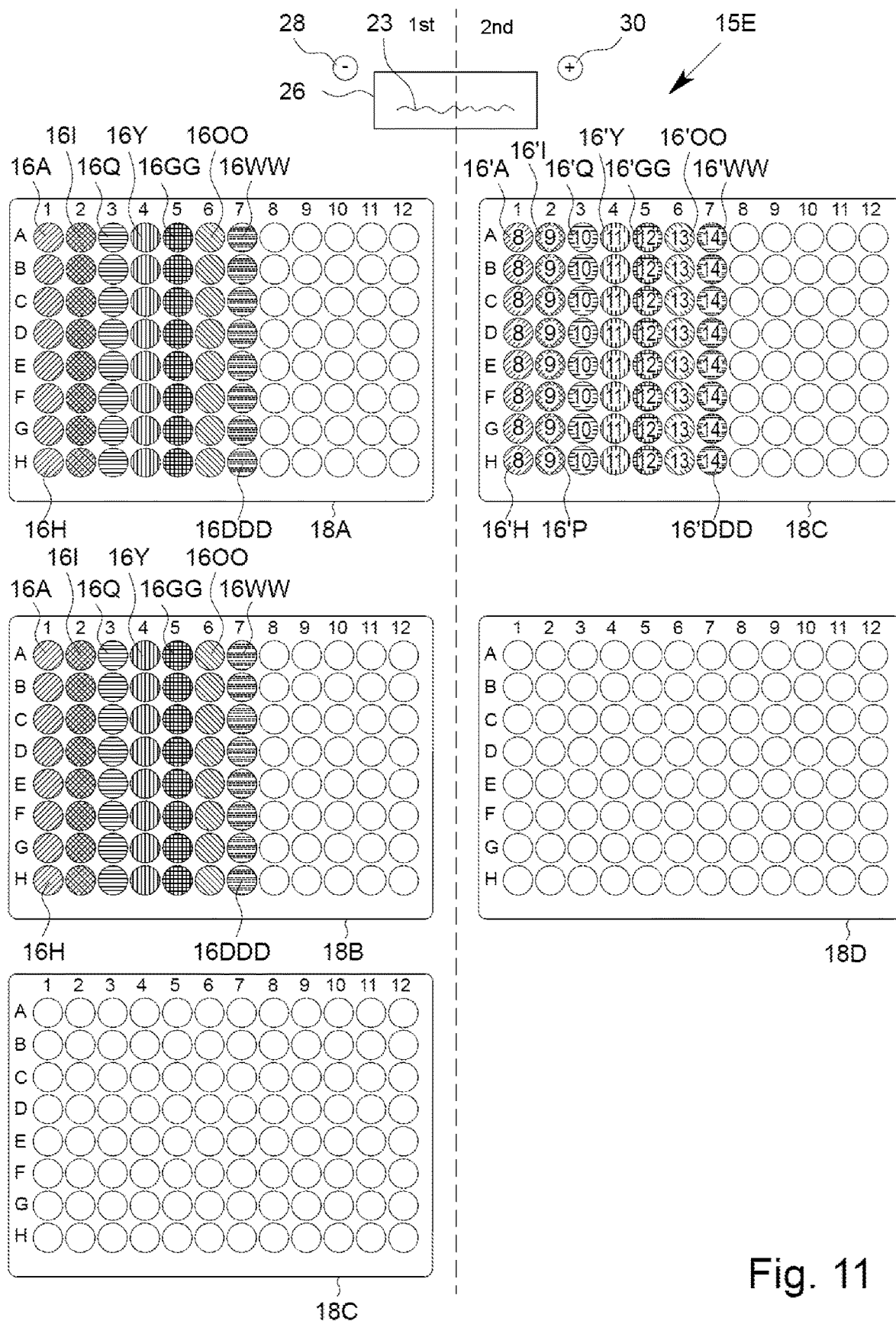
FIG. 11 is a schematic plan view of the fifth configuration interface from FIG. 10 in a second state.

FIG. 11 shows a schematic depiction of a second state of the fifth configuration interface 15E from FIG. 10. The configuration interface 15E presents the pipetting unit equivalent 18A in the state from FIG. 10. Additionally, multiple source wells 16A to 16DDD are presented on the pipetting unit equivalent 18B (as second source plate) on the 1st side. The higher numbers "8" to "14" in the destination wells 16'A to 16'DDD of the pipetting unit equivalent 18C in comparison with FIG. 10 indicate that additional transfer steps are specified in regard to these destination wells.

Specifically, in an eighth transfer step, the multichannel pipetting apparatus 4 is supposed to be used to simultaneously receive liquids 6 from the receptacle devices 5 that correspond to the source wells 16A to 16H of the pipetting unit equivalent 18B (as second source plate). In this transfer step, the liquids 6 are supposed to be delivered to the receptacle devices 5 that correspond to the destination wells 16'A to 16'H of the pipetting unit equivalent 18C. In the ninth transfer step, the multichannel pipetting apparatus 4 is supposed to be used to simultaneously receive liquids 6 from the receptacle devices 5 that correspond to the source wells 16I to 16P of the pipetting unit equivalent 18B. In this second transfer step, the liquids 6 are supposed to be delivered to the receptacle devices 5 that correspond to the destination wells 16'I to 16'P of the pipetting unit equivalent 18C. The same applies to the remainder of the transfer steps.

Considered overall, the liquids 6 of the receptacle devices 5 that correspond to the source wells 16A to 16H of the pipetting unit equivalent 18A are mixed with the liquids 6 of the receptacle devices 5 that correspond to the source wells 16A to 16H of the pipetting unit equivalent 18B, specifically in the receptacle devices 5 that correspond to the destination wells 16'A to 16'H of the pipetting unit equivalent 18C.

Figure 12:
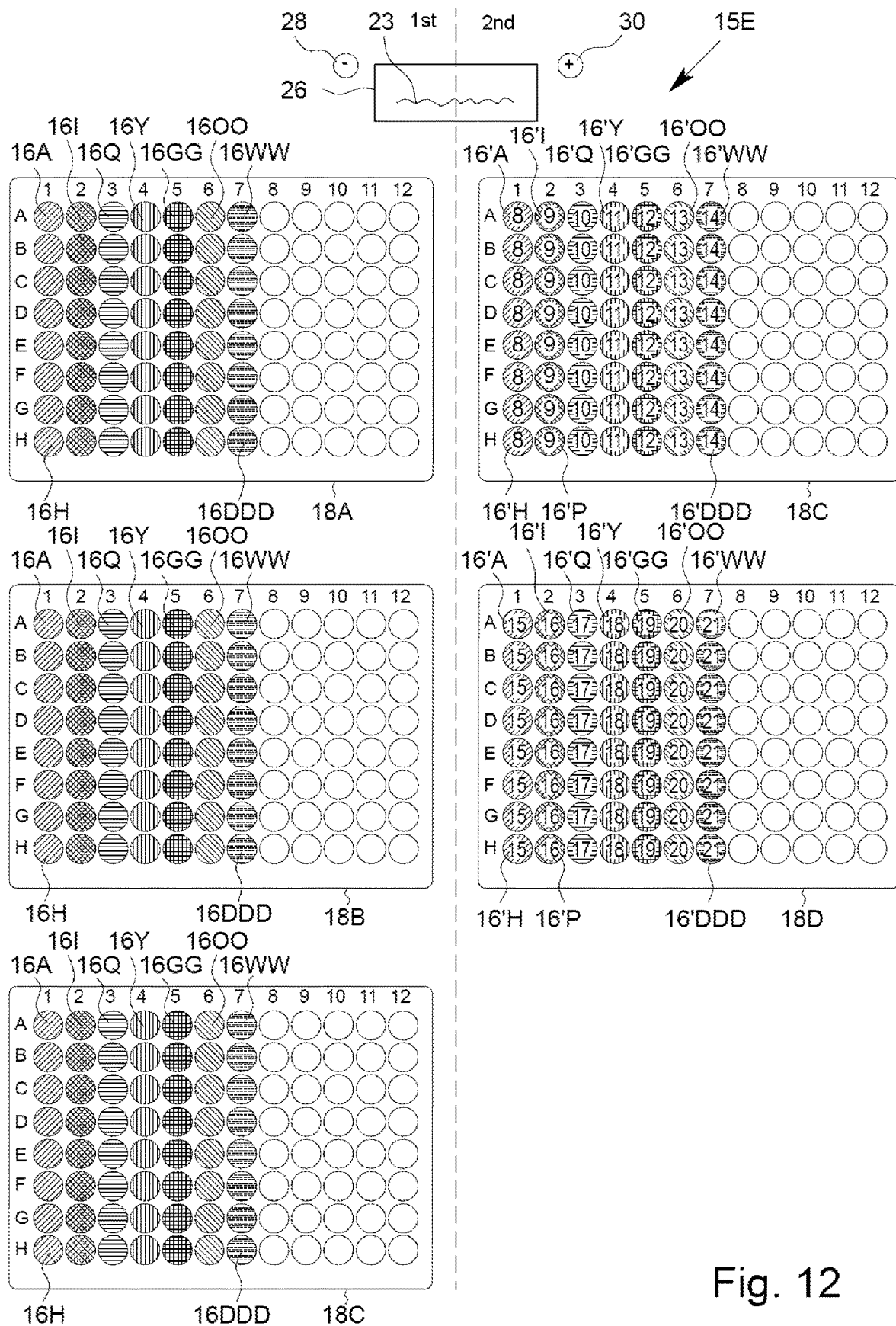
FIG. 12 is a schematic plan view of the fifth configuration interface from FIG. 10 in a third state.

FIG. 12 shows a schematic depiction of a third state of the fifth configuration interface 15E from FIG. 10. The configuration interface 15E presents the pipetting unit equivalents 18A and 18B in the state from FIG. 11.

In this example, the liquids 6 available as mixtures in the receptacle devices 5 that correspond to the destination wells 16'A to 16'H of the pipetting unit equivalent 18C are supposed to be transferred to receptacle devices 5 that correspond to destination wells 16'A to 16'H of a pipetting unit equivalent 18D (as second destination plate). The pipetting unit that corresponds to the pipetting unit equivalent 18C previously acting as destination plate now serves as source (of the liquids 6 available as mixtures) and hence the pipetting unit equivalent 18C now serves as source plate.

Multiple source wells 16A to 16DDD are thus selected and presented on the pipetting unit equivalent 18C (now as third source plate) on the 1st side. Multiple destination wells 16'A to 16'DDD are selected and presented on the pipetting unit equivalent 18D (as second destination plate) on the 2nd side. The numbers "15" to "21" in the destination wells 16'A to 16'DDD of the pipetting unit equivalent 18D indicate the order of the transfer steps additionally specified in this state.

In a 15th transfer step, the multichannel pipetting apparatus 4 is supposed to be used to simultaneously receive the mixed liquids 6 from the receptacle devices 5 that correspond to the source wells 16A to 16H of the pipetting unit equivalent 18C. In this transfer step, the mixed liquids 6 are supposed to be delivered to the receptacle devices 5 that correspond to the destination wells 16'A to 16'H of the pipetting unit equivalent 18D. In the 16th transfer step, the multichannel pipetting apparatus 4 is supposed to be used to simultaneously receive the mixed liquids 6 from the receptacle devices 5 that correspond to the source wells 16I to 16P of the pipetting unit equivalent 18C. In this second transfer step, the mixed liquids 6 are supposed to be delivered to the receptacle devices 5 that correspond to the destination wells 16'I to 16'P of the pipetting unit equivalent 18D. The same applies to the remainder of the transfer steps.

In the preferred exemplary embodiment depicted, the control device 1 is designed to control the multichannel pipetting apparatus 4 and the actuator 3 such that, after a transfer step with one liquid 6 and before a subsequent transfer step with a different liquid 6, a change of all pipette tips 7 of the multichannel pipetting apparatus 4 is performed.

Therefore, in the example depicted in FIG. 12, all eight pipette tips 7 of the multichannel pipetting apparatus 4 would be replaced after every transfer step. All in all, there would be 21 changes of eight pipette tips 7 each time. Thus, 168 pipette tips would be thrown away. The journeys to the waste bin 32, to the pipette tip holders 34 and back from each are time-consuming.

Figure 13:
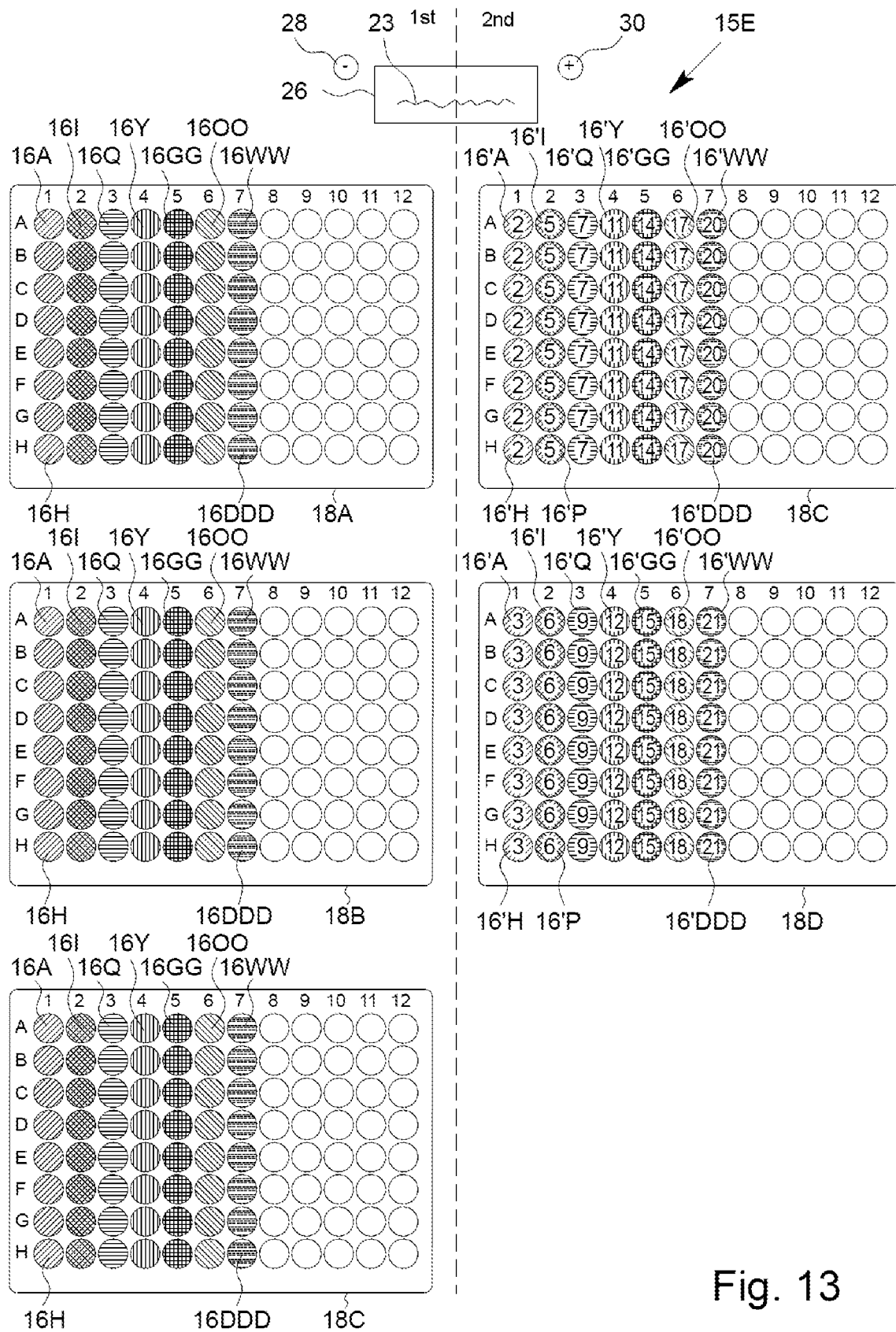
FIG. 13 is a schematic plan view of the fifth configuration interface from FIG. 10 in a fourth state.

FIG. 13 shows a schematic depiction of a fourth state of the fifth configuration interface 15E from FIG. 10. Using the context menu or else another method, preferably provided for in the configuration interface 15E, there is the option of it preferably being selectable or selected that the control device 1 automatically alters the order of execution of these transfer steps such that transfer steps in accordance with which liquid 6 is supposed to be delivered to the same receptacle device 5 and the resultant liquid 6 is supposed to be received from this receptacle device 5 and delivered to a different receptacle device 5 are immediately successive.

In this exemplary embodiment too, the control device 1 is designed so as, before the execution of the specified transfer steps by the multichannel pipetting apparatus 4 and the actuator 3, to analyze the specified order of execution of these transfer steps and the liquids 6 to be pipetted in these transfer steps. In the present exemplary embodiment, during the analyzing, the control device 1 looks for transfer steps in accordance with which compatible liquids 6 need to be pipetted. During the analyzing of the transfer steps in accordance with FIG. 12, the control device 1 will find that liquids 6 to be mixed need to be pipetted in accordance with transfer steps 1 and 8 and the thus mixed liquids 6 need to be pipetted in accordance with transfer step 15. This also applies accordingly to transfer steps 2, 9, 16 and 3, 10, 17 etc. These transfer steps with compatible liquids 6 are depicted using the same shading in FIG. 12.

During the analyzing, the specified transfer steps are additionally examined by the control device 1 to ascertain whether these transfer steps are independent of other transfer steps or whether the execution of these transfer steps can take place in an order other than that specified. In the example shown in FIG. 12, the transfer steps 1 and 8 need to take place before transfer step 15. Accordingly, the transfer steps 2 and 9 need to take place before transfer step 16, etc.

The control device 1 is now designed such that, after the analysis, it automatically alters the order of execution of these analyzed transfer steps, specifically such that transfer steps in accordance with which liquid 6 is supposed to be delivered to the same receptacle device 5 and the resultant liquid 6 is supposed to be received from this receptacle device 5 and delivered to a different receptacle device 5 are immediately successive. The resultant changed order is depicted in FIG. 13 and discernible from the respective number in the destination wells 16'A to 16'DDD in the pipetting unit equivalents 18C and 18D.

For example, the transfer step previously specified as eighth transfer step now needs to be executed as second transfer step. The transfer step previously specified as 15th transfer step now needs to be executed as third transfer step. The transfer step previously specified as seventh transfer step now needs to be executed as 19th transfer step. The transfer step previously specified as 14th transfer step now needs to be executed as 20th transfer step. The transfer step previously specified as 21st transfer step still needs to be executed as 21st transfer step.

As a result of the changed order of execution of the transfer steps, only seven instead of 21 changes of eight pipette tips 7 each time are performed here, namely after transfer steps 3, 6, 9, 12, 15, 18 and 21. This saves materials (pipette tips 7) and time (for the journeys to the waste bin 32 and back). As such, instead of 168 pipette tips 7, only 56 pipette tips 7 are changed and thrown away here.

The aspects described above are preferably combinable. Further, there can be provision for the principles explained in association with the configuration interfaces 15B to 15L to be selectable as different options and/or by means of one or more context menus in the same configuration interface. To this end, there can be provision in particular for virtual switches, checkboxes, drop-down menus, soft buttons or the like. Further, it is preferred both for wells 16A to 16F to be selectable and for the context menu to be generable and, in this way or in another way, one or more options to be selectable or configurable in the same configuration interface 15B to 15L, preferably with one or more volume difference(s), volumes, target volumes and/or the combination, splitting or a changed arrangement being stipulable, settable or activable.

The present invention also relates to a method for controlling the automated pipetting system 2 using the control device 1, wherein the principles described above are performed on their own or in combination. Preferably, this involves an input by means of the input device 10 being interpreted by the control device 1 such that selectable wells 16, 16' are selected in part, individually or in groups, in particular by moving the selection tool 22 and inputting during this and/or subsequently to this, for example by means of a switch or button. The control device 1 preferably interprets this as selection of the respective well 16, 16' or of an applicable first or second group 27, 29 and preferably executes individual or a combination of steps for which the control device 1 has been described as suitable above.

Further, it is preferred for the method to comprise control of the automated pipetting system 2. To this end, there can be provision for the control device 1 to control the different selections of wells 16, 16', particularly preferably in the respective chronological order of the selection and taking into consideration the respective options active during the selection, by virtue of the control device 1 generating machine commands and transmitting them to the automated pipetting system 2.

What is claimed is:

1. A control device for controlling an automated pipetting system, wherein:
   the control device is computer-implemented,
   the control device is configured to control at least one actuator for moving a pipetting apparatus between receptacle devices for liquids that are to be pipetted,
   the control device is configured to control the pipetting apparatus in such a way that a specific transfer volume of liquid can be taken up from at least one of the receptacle devices, and at least a portion of the transfer volume of liquid can be dispensed into at least one other of the receptacle devices by means of the pipetting apparatus in a transfer step,
   the control device has an input device, and
   the control device has a display device with which at least one configuration interface is displayable, the configuration interface representing the receptacle devices as graphically depicted wells,
   the receptacle devices from which liquid to be pipetted is to be taken up by the pipetting apparatus being represented as source wells, and the receptacle devices to which liquid to be pipetted is to be dispensed by the pipetting apparatus is depicted as destination wells,
   multiple source wells and multiple destination wells are selectable in the configuration interface by means of the input device,
   multiple transfer steps and an order of execution thereof by the pipetting apparatus and the actuator are specifiable with the configuration interface,
   before the execution of the multiple specified transfer steps by the pipetting apparatus and the actuator, the control device is configured to analyze the specified order of execution of the transfer steps and the liquid to be pipetted in the transfer steps, and to automatically act to reduce material consumption and/or time required for the execution of the specified transfer steps by at least one of altering the order of execution of the transfer steps or combining multiple instances of the transfer steps based on results of said analysis,
   wherein the control device is adapted to determine transfer steps with compatible liquids during the analysis of the transfer steps, and wherein the display device is adapted to display at least one of the source or destination wells having compatible liquids in the configuration interface in a visually distinguishable manner and
   wherein the control device is adapted to be able to alter the order of execution of the transfer steps automatically such that transfer steps in accordance with which liquid is supposed to be taken up from the same source receptacle device or dispensed into the same destination receptacle device are to be performed immediately successively or the control device is adapted to be able to alter the order of execution of the transfer steps automatically such that transfer steps in accordance with which liquid is supposed to be dispensed into the same destination receptacle device and liquid supposed to be taken up from that receptacle device and dispensed into a different destination receptacle device are performed immediately successively.

2. The control device according to claim 1, wherein the control is adapted to be able to automatically combine transfer steps by automatically replacing transfer steps, in accordance with which a specific transfer volume of liquid is to be taken up from the same source receptacle device and dispensed into a specific destination receptacle device, with a combined transfer step in which the sum of the transfer volumes of liquid is to be taken up from the source receptacle device of the respective transfer steps on a single occasion and the respective specific transfer volume of liquid is to be dispensed into the specific destination receptacle device.

3. The control device according to claim 1, wherein the control device is adapted to enable automatic combining of transfer steps by automatically replacing transfer steps, in accordance with which a specific transfer volume of liquid is to be taken up from specific source receptacle devices and dispensed into the same destination receptacle device with a combined transfer step in which the respective specific transfer volume of liquid is to be taken up from the respective source receptacle devices in immediate succession and equal the sum of the specific transfer volumes of liquid is to be dispensed into the destination receptacle device on a single occasion.

4. The control device according to claim 1, wherein the display device is adapted to be able to display at least one of an altered order of the transfer steps or a changed transfer volume in the configuration interface, or to display the sequence of the transfer steps in a second configuration interface.

5. The control device according to claim 1, wherein the control device is adapted to be able to control the pipetting apparatus and the actuator such that a change of pipette tip of the pipetting apparatus is performed at least one of:
immediately after a combined transfer step or
after a transfer step with one liquid and before a subsequent transfer step with a different liquid.

6. The control device according to claim 1, wherein before or after the analysis of the transfer steps, transfer steps are excludable from the analysis of the control device, or multiple different liquids are selectable as needing to be mixed for the analysis of the transfer steps, in the configuration interface by means of the input device.

7. An automated pipetting system having a control device according to claim 1, wherein the pipetting system has at least one actuator for moving a pipetting apparatus between receptacle devices for liquids that are to be pipetted, the actuator being controllable by the control device.

8. A method for controlling an automated pipetting system by means of a control device to control at least one actuator for moving a pipetting apparatus between source and destination receptacle devices for liquids that are to be pipetted, the control device having an input device and a display device for displaying at least one configuration interface, the method comprising:
using the control device to control the pipetting apparatus such that a specific transfer volume of liquid can be taken up from at least one source receptacle device, and at least a portion of the transfer volume of liquid can be dispensed into at least one destination receptacle device by means of the pipetting apparatus in a transfer step,
representing the receptacle devices in the configuration interface by graphically depicted wells, the receptacle devices from which liquid to be pipetted is to be taken up by the pipetting apparatus being represented as source wells, and the receptacle devices in to which liquid to be pipetted is to be dispensed by the pipetting apparatus being represented as destination wells,
selecting multiple source wells and multiple destination wells in the configuration interface by means of the input device,
specifying multiple transfer steps and the order of execution thereof by the pipetting apparatus and the actuator, and assigning multiple previously selected source wells in the configuration interface to at least one destination well by selecting this destination well, wherein:
before execution of multiple specified transfer steps by the pipetting apparatus and the actuator, the control device is used to perform an analysis of a specified order of execution of the transfer steps and the liquid to be pipetted in the transfer steps and
after the analysis, the control device automatically acts to reduce material consumption and/or time required for the execution of the specified transfer steps by at least one altering the order of execution of the transfer steps or combining multiple instances of the transfer steps,
wherein the control device determines transfer steps with compatible liquids during the analysis, and wherein the display device displays any source or destination wells having compatible liquids in the configuration interface in a visually distinguishable manner, wherein the control device alters the order of execution of these transfer steps automatically in accordance with which liquid is supposed to be taken up from the same source receptacle device or dispensed into the same destination receptacle device are performed immediately successively or wherein the control device alters the order of execution of these transfer steps automatically such that transfer steps in accordance with which liquid is supposed to be dispensed into the same destination receptacle device and liquid to be taken up from this destination receptacle device and dispensed into a different destination receptacle device are performed immediately successively.

9. The method according to claim 8, wherein the control device combines transfer steps by automatically replacing transfer steps, in accordance with which a specific transfer volume of liquid is to be taken up from the same source receptacle device and dispensed into a specific destination receptacles device, a combined transfer step in accordance with which the sum of the transfer volumes of liquid is to be taken up from the source receptacle device of the respective transfer steps on a single occasion and the respective specific transfer volume of liquid is to be dispensed into the specific destination receptacle device.

10. The method according to claim 8, wherein the control device combines transfer steps by automatically replacing transfer steps in accordance with which a specific transfer volume of liquid to be taken up from specific source receptacles devices and dispensed into the same destination receptacle device with a combined transfer step in which the respective specific transfer volumes of liquid is to be taken up from the respective source receptacle devices in immediate succession and the sum of the specific transfer volumes of liquid is to be dispensed into the destination receptacle device on a single occasion.

11. The method according to claim 8, wherein the display device displays at least one of the altered order of the transfer steps or a changed transfer volume in the configuration interface.

12. The method according to claim 8, wherein the control device controls the pipetting apparatus and the actuator to perform a change of pipette tip of the pipetting apparatus at least one of:
immediately after a combined transfer step or
after a transfer step with one liquid and before a subsequent transfer step with a different liquid.

13. The method according to claim 8, wherein the input device is used to at least one of exclude transfer steps from the analysis, or to select multiple different liquids to be mixed for the analysis of the transfer steps.

14. The method according to claim 8, wherein a pipette tip of the pipetting apparatus that has already been used and is contaminated by different types of liquid is reused for at least one further transfer step.

* * * * *